US009149424B2

(12) United States Patent
Mehal et al.

(10) Patent No.: US 9,149,424 B2
(45) Date of Patent: Oct. 6, 2015

(54) COMPOSITIONS AND METHODS FOR REDUCING HEPATOTOXICITY ASSOCIATED WITH DRUG ADMINISTRATION

(75) Inventors: Wajahat Mehal, Guilford, CT (US); Avlin Imaeda, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 671 days.

(21) Appl. No.: 12/734,153

(22) PCT Filed: Oct. 20, 2008

(86) PCT No.: PCT/US2008/011945
§ 371 (c)(1),
(2), (4) Date: Jul. 6, 2010

(87) PCT Pub. No.: WO2009/051840
PCT Pub. Date: Apr. 23, 2009

(65) Prior Publication Data
US 2010/0297271 A1 Nov. 25, 2010

Related U.S. Application Data

(60) Provisional application No. 60/999,413, filed on Oct. 18, 2007.

(51) Int. Cl.
*A61K 31/198* (2006.01)
*A61K 31/60* (2006.01)
*A61K 45/06* (2006.01)
*A61K 9/02* (2006.01)
*A61K 9/00* (2006.01)

(52) U.S. Cl.
CPC ............ *A61K 9/0019* (2013.01); *A61K 31/198* (2013.01); *A61K 31/60* (2013.01); *A61K 45/06* (2013.01); *A61K 9/0014* (2013.01); *A61K 9/0031* (2013.01); *A61K 9/0046* (2013.01); *A61K 9/0048* (2013.01); *A61K 9/0073* (2013.01); *A61K 9/02* (2013.01)

(58) Field of Classification Search
CPC ... A61K 9/0019; A61K 9/006; A61K 9/0014; A61K 31/616; A61K 45/06; A61K 31/60; A61K 31/198; A61K 9/0031; A61K 9/0046; A61K 9/0048; A61K 9/0073
See application file for complete search history.

(56) References Cited

U.S. PATENT DOCUMENTS

| 3,773,929 A | 11/1973 | Huber et al. |
| 2004/0127470 A1 | 7/2004 | Masferrer |
| 2005/0148554 A1 | 7/2005 | Zhang et al. |
| 2005/0158302 A1 | 7/2005 | Faustman et al. |
| 2009/0239831 A1 | 9/2009 | Mehal et al. |
| 2010/0016262 A1 | 1/2010 | Mehal et al. |
| 2011/0135602 A1 | 6/2011 | Ivanov et al. |
| 2011/0256130 A1 | 10/2011 | Schultz et al. |
| 2012/0115782 A1 | 5/2012 | Mehal et al. |
| 2012/0225931 A1 | 9/2012 | Mehal et al. |

FOREIGN PATENT DOCUMENTS

| WO | 2010121128 A2 | 10/2010 |
| WO | 2011041311 A2 | 4/2011 |

OTHER PUBLICATIONS

Kimura et al. "Metallothionein Acts as a Cytoprotectant against Doxorubicin Toxicity". JPET 292: 299-302, 2000.*
Timothy P. Reilly, et al., "A Protective Role for Cylcooxygenase-2 in Drug-induced Liver Injury in Mice." Toxicology, vol. 14, No. 12, pp. 1620-1628, 2001 ISSN 0893-228X.
J. De Vries, et a., "Protective against paracetamol-induced hepatotoxicity by acetylsalicylic acid in rats", Toxicology, vol. 30, No. 4, pp. 297-304, 1984, ISSN 0300-483X.
L.W. Whitehouse, et al., "Effect of acetylsalicylic acid on toxic doses of acetaminophen in the mouse", Toxicology and Applied Pharmacology, vol. 38, No. 3, pp. 571-582, 1976, ISSN 0041-008X.
Krysko DV, Kaczmarek A, Krysko O, Heyndrickx L, Woznicki J, Bogaert P, Cauwels A, Takahashi N, Magez S, Bachert C, Vandenabeele P. TLR-2 and TLR-9 are sensors of apoptosis in a mouse model of doxorubicin-induced acute inflammation. Cell Death and Differentiation, 2001;18:1316-1325.
Kaplowitz N, Kuhlenkamp J, Goldstein L, Reeve J. Effect of Salicylates and Phenobarbital on Hepatic Glutathione in the Rat. J Pharm and Exp Ther 1979;212:240-45.
Sjoholm A et al.; Inflammation and the etiology of type 2 diabetes. Diabetes/metabolism Research and Reviews 2006; 22:4-10.
Trujillo-Murillo K et al.; Acetylsaliclic Aacid Inhibits Hepatitis C Virus RNA and Protein Expression Through Cyclooxygenase 2 Signaling Pathways. Hepatology 2008; 47:14262-14272.
Denda A et al.; Prevention by acetylsalicylic acid of liver cirrhosis and carcinogenesis as well as generations of 8-hydroxyguanosine and thiobarbituric acid-reactible substances caused by a choline-deficient, L-amino acid-denied diet in rats. Carcinogenesis. 1994; 15:1279-1283.
Imaeda AB et al.; Acetaminophen-induced hepatotoxicity in mice is dependent on Tlr9 and the Nalp3 inflammasome. J. Clin. Invest. 2009; 119:305-314.

(Continued)

*Primary Examiner* — Renee Claytor
(74) *Attorney, Agent, or Firm* — Henry D. Coleman; R. Neil Sudol

(57) ABSTRACT

The present invention relates to the discovery that acetylsalicylic acid (ASA or aspirin), salicylic acid (SA) and related salicylate esters and their pharmaceutically acceptable salts, when coadministered in effective amounts with a drug or other bioactive agent which typically (in the absence of the salicylate compound) produces significant hepatotoxicity as a secondary indication, will substantially reduce or even eliminate such hepatotoxicity. Favorable therapeutic intervention results from the use of the present invention having the effect of reducing hepatotoxicity associated with the administration of certain drugs and other bioactive agents and in certain instances of allowing the administration of higher doses of a compound which, without the coadministration, would produce hepatotoxicity which limits or even negates the therapeutic value of the compound.

21 Claims, 13 Drawing Sheets

(56) References Cited

OTHER PUBLICATIONS

Assy N et al.; The Beneficial Effect of Aspirin and Enoxaparin on Fibrosis Progression and Regenerative Activity in a Rat Model of Cirrhosis. Dig Dis Sci 2007; 52:1187-1193.

Sahasrabuddhe VV et al.; Nonsteroidal Anti-inflammatory Drug Use, Chronic Liver Disease, and Hepatocellular Carcinoma. J Natl Cancer Inst Nov. 28, 2012; pp. 1-7.

Kimura et al.; Metallothionein acts as a cytoprotectant against doxorubicin toxicity. JPET 2000; 292: 299-302.

Krysko DV et al.; TLR-2 and TLR-9 are sensors of apoptosis in a mouse model of doxorubicin-induced acute inflammation. Cell Death and Differentiation 2001; 18:1316-1325.

Kaplowitz N et al.; Effect of Salcylates and Phenobarbital on Hepatic Glutathione in the Rat. J Pharm and Exp Ther 1979; 212:240-245.

Han D et al.; Mechanisms of Liver Injury. III. Role of glutathione redox status in liver injury. Am J Physiol Gastrointest Liver Physiol 2006; 291: G1-G7.

Piemonte F et al.; Protein glutathionylation increases in the liver of patients with non-alcoholic fatty liver disease. Journal of Gastroenterology and Hepatology 2008; 23: e457-e464. Epub Aug. 6, 2007.

Encke et al.; Immunosuppression and modulation in liver transplantation. Nephrol Dial Transplant 2004; 19(Suppl 4): iv22-iv25.

Giboney et al.; Mildly Elevated Live Transaminase Levels in the Asymptomatic Patient. Am Fam Physician 2005; 71: 1105-10.

Kaneda et al.; Inflammatory Liver Steatosis Caused by IL-12 and IL-18. Journal of Interferon & Cytokine Research 2003; 23: 155-162.

Fox JM; Kombinationsarzneimittel aus Paracetamol plus Acetylsalicylsaure: Nutzen and Risken [Combination analgesics consisting of paracetamol plus acetylsalicylic acid: Benefits and Risks] SCHMERZ Nov. 1, 1995; 9:273-285.

Grennan DM et al.; The Aspirin-Ibuprofen Interaction in Rheumatoid Arthritis. Br J Clin Pharmac Jan. 1, 1979; pp. 497-503.

Does Aspirin Harm the Liver? The Lancet Apr. 1, 1974 ; 303:667 Abstract. XP055077832.

Imaeda AB et al.; 467 Aspirin Blocks Acetaminophen Induced Hepatotoxicity and Mortality in Mice-Dependent on the ACS/Caspase-1 Inflammasome. Gastroenterology Apr. 1, 2008; 134:A-767.

Database WPI Week 200347; Thompson Scientific, London, GB; AN 2003-500900; XP002712530, & KR 2002 0007566 A (Samjin Pharm Co Ltd) Jan. 29, 2002. Abstract.

Database Biosis [Online] Biosciences Information Service, Philadelphia, PA, US Oct. 2004, Carroll CL et al; Better medication adherence results in greater improvement in severity of psoriasis. XP02712346, Database accession No. PREV200500038983. Abstract. & Carroll CL et al.Better medication adherence results in greater improvement in severity ofpsoriasis. British Journal of Dermatology Oct. 2004; 151:895-897.

Database Embase [Online]; Elsevier Science Publishers, Amsterdam, NL; 1982, Shaw JFL: Combined effects of cyclosporin A and sodium salicylate upon survival of rat heart allografts. XP002712347, Database accession No. EMB-1982249805 *abstract* & Shaw JFL; Combined effects of cyclosporin A and sodium salicylate upon survival of rat heart allografts. IRCS Medical Science 1982 GB 1982; 10:827.

Miura K et al.; Toll-Like Receptor 9 Promotes Steatohepatitis by Induction of Interleukin-1beta in mice. Gastroenterology 2010; 139:323-334.

Genovese MC; Fever, Rash, and Arthritis in a Woman With Silicone Gel Breast Implants; Western J Med 1997; 167:149-158.

Hunt BJ et al.; Endothelial Cell Activation a central pathophysiological process; British Med J 1998; 316:1328-1329.

Yu D et al.; Modifications Incorporated in CpG Motifs of OLigodeoxynucleotides Lead to Antagonist Activity of Toll-like Receptors 7 and 9; J. Med. Chem. 2009; 52:5108-5114.

Wang D et al.; Oligodeoxyribonucleotide-Based Antagonists for Toll-Like Receptors 7 and 9; J. Med. Chem. 2009; 52:551-558.

Lee, W.M. 2007. Acetaminophen toxicity: changing perceptions on a social/medical issue. Hepatology 46:966-970.

Kaplowitz, N. 2004. Acetaminophen hepatotoxicity: what do we know, what don't we know, and what do we do next? Hepatology 40:23-26.

Liu, Z.X., Han, D., Gunawan, B., and Kaplowitz, N. 2006. Neutrophil depletion protects against murine acetaminophen hepatotoxicity. Hepatology 43:1220-1230.

Liu, Z.X., Govindarajan, S., and Kaplowitz, N. 2004. Innate immune system plays a critical role in determining the progression and severity of acetaminophen hepatotoxicity. Gastroenterology 127:1760-1774.

Cover, C., Liu, J., Farhood, A., Malle, E., Waalkes, M.P., Bajt, M.L., and Jaeschke, H. 2006. Pathophysiological role of the acute inflammatory response during acetaminophen hepatotoxicity. Toxicol Appl Pharmacol 216:98-107.

Fiorucci, S., Antonelli, E., Mencarelli, A., Palazzetti, B., Alvarez-Miller, L., Muscara, M., del Soldato, P., Sanpaolo, L., Wallace, J.L., and Morelli, A. 2002. A No-releasing derivative of acetaminophen spares the liver by acting at several checkpoints in the Fas pathway. Br J Pharmacol 135:589-599.

Chen, C.J., Kono, H., Golenbock, D., Reed, G., Akira, S., and Rock, K.L. 2007. Identification of a key pathway required for the sterile inflammatory response triggered by dying cells. Nat Med 13:851-856.

Mariathasan, S., Newton, K., Monack, D.M., Vucic, D., French, D.M., Lee, W.P., Roose-Girma, M., Erickson, S., and Dixit, V.M. 2004. Differential activation of the inflammasome by caspase-1 adaptors ASC and Ipaf. Nature 430:213-218.

Martinon, F., Burns, K., and Tschopp, J. 2002. The inflammasome: a molecular platform triggering activation of inflammatory caspases and processing of proIL-beta. Mol Cell 10:417-426.

Ogura, Y., Sutterwala, F.S., and Flavell, R.A. 2006. The inflammasome: first line of the immune response to cell stress. Cell 126:659-662.

Vollmer, J. 2006. TLR9 in health and disease. Int Rev Immunol 25:155-181.

Lamphier, M.S., Sirois, C.M., Verma, A., Golenbock, D.T., and Latz, E. 2006. TLR9 and the recognition of self and non-self nucleic acids. Ann N Y Acad Sci 1082:31-43.

Enari, M., Sakahira, H., Yokoyama, H., Okawa, K., Iwamatsu, A., and Nagata, S. 1998. A caspase-activated DNase that degrades DNA during apoptosis, and its inhibitor ICAD. Nature 391:43-50.

Huck, S., Deveaud, E., Namane, A., and Zouali, M. 1999. Abnormal DNA methylation and deoxycytosine-deoxyguanine content in nucleosomes from lymphocytes undergoing apoptosis. Faseb J 13:1415-1422.

Lunec, J., Herbert, K., Blount, S., Griffiths, H.R., and Emery, P. 1994. 8-Hydroxydeoxyguanosine. A marker of oxidative DNA damage in systemic lupus erythematosus. FEBS Lett 348:131-138.

Rifkin, I.R., Leadbetter, E.A., Busconi, L., Viglianti, G., and Marshak-Rothstein, A. 2005. Toll-like receptors, endogenous ligands, and systemic autoimmune disease. Immunol Rev 204:27-42.

Mariathasan, S., and Monack, D.M. 2007. Inflammasome adaptors and sensors: intracellular regulators of infection and inflammation. Nat Rev Immunol 7:31-40.

Barrat, F.J., Meeker, T., Chan, J.H., Guiducci, C., and Coffman, R.L. 2007. Treatment of lupus-prone mice with a dual inhibitor of TLR7 and TLR9 leads to reduction of autoantibody production and amelioration of disease symptoms. Eur J Immunol 37:3582-3586.

Barrat, F.J., Meeker, T., Gregorio, J., Chan, J.H., Uematsu, S., Akira, S., Chang, B., Duramad, O., and Coffman, R.L. 2005. Nucleic acids of mammalian origin can act as endogenous ligands for Toll-like receptors and may promote systemic lupus erythematosus. J Exp Med 202:1131-1139.

Dinarello, C.A. 2007. Interleukin-18 and the pathogenesis of inflammatory diseases. Semin Nephrol 27:98-114.

Pirhonen, J., Sareneva, T., Kurimoto, M., Julkunen, I., and Matikainen, S. 1999. Virus infection activates IL-1 beta and IL-18 production in human macrophages by a caspase-1-dependent pathway. J Immunol 162:7322-7329.

(56) References Cited

OTHER PUBLICATIONS

Kalina, U., Koyama, N., Hosoda, T., Nuernberger, H., Sato, K., Hoelzer, D., Herweck, F., Manigold, T., Singer, M.V., Rossol, S., et al. 2002. Enhanced production of IL-18 in butyrate-treated intestinal epithelium by stimulation of the proximal promoter region. *Eur J Immunol* 32:2635-2643.

Watanabe, A., Hashmi, A., Gomes, D.A., Town, T., Badou, A., Flavell, R.A., and Mehal, W.Z. 2007. Apoptotic hepatocyte DNA inhibits hepatic stellate cell chemotaxis via toll-like receptor 9. *Hepatology* 46:1509-1518.

Martin-Armas, M., Simon-Santamaria, J., Pettersen, I., Moens, U., Smedsrod, B., and Sveinbjornsson, B. 2006. Toll-like receptor 9 (TLR9) is present in murine liver sinusoidal endothelial cells (LSECs) and mediates the effect of CpG-oligonucleotides. *J Hepatol* 44:939-946.

Traggiai, E., Chicha, L., Mazzucchelli, L., Bronz, L., Piffaretti, J.C., Lanzavecchia, A., and Manz, M.G. 2004. Development of a human adaptive immune system in cord blood cell-transplanted mice. *Science* 304:104-107.

Puren, A.J., Fantuzzi, G., and Dinarello, C.A. 1999. Gene expression, synthesis, and secretion of interleukin 18 and interleukin 1beta are differentially regulated in human blood mononuclear cells and mouse spleen cells. *Proc Natl Acad Sci U S A* 96:2256-2261.

Martinon, F., Petrilli, V., Mayor, A., Tardivel, A., and Tschopp, J. 2006. Gout-associated uric acid crystals activate the NALP3 inflammasome. *Nature* 440:237-241.

Wu, K.K., Liou, J.Y., and Cieslik, K. 2005. Transcriptional Control of COX-2 via C/EBPbeta. *Arterioscler Thromb Vasc Biol* 25:679-685.

Reilly, T.P., Brady, J.N., Marchick, M.R., Bourdi, M., George, J.W., Radonovich, M.F., Pise-Masison, C.A., and Pohl, L.R. 2001. A protective role for cyclooxygenase-2 in drug-induced liver injury in mice. *Chem Res Toxicol* 14:1620-1628.

Wu, K.K. 2003. Aspirin and other cyclooxygenase inhibitors: new therapeutic insights. *Semin Vasc Med* 3:107-112.

Viglianti, G.A., Lau, C.M., Hanley, T.M., Miko, B.A., Shlomchik, M.J., and Marshak-Rothstein, A. 2003. Activation of autoreactive B cells by CpG dsDNA. *Immunity* 19:837-847.

Tsutsui, H., Matsui, K., Okamura, H., and Nakanishi, K. 2000. Pathophysiological roles of interleukin-18 in inflammatory liver diseases. *Immunol Rev* 174:192-209.

Pomerantz, B.J., Reznikov, L.L., Harken, A.H., and Dinarello, C.A. 2001. Inhibition of caspase 1 reduces human myocardial ischemic dysfunction via inhibition of IL-18 and IL-1beta. *Proc Natl Acad Sci U S A* 98:2871-2876.

Akahoshi, T., Murakami, Y., and Kitasato, H. 2007. Recent advances in crystal-induced acute inflammation. *Curr Opin Rheumatol* 19:146-150.

Duncan, J.A., Bergstralh, D.T., Wang, Y., Willingham, S.B., Ye, Z., Zimmermann, A.G., and Ting, J.P. 2007. Cryopyrin/NALP3 binds ATP/dATP, is an ATPase, and requires ATP binding to mediate inflammatory signaling. *Proc Natl Acad Sci U S A* 104:8041-8046.

Tsujimoto, H., Ono, S., Matsumoto, A., Kawabata, T., Kinoshita, M., Majima, T., Hiraki, S., Seki, S., Moldawer, L.L., and Mochizuki, H. 2006. A critical role of CpG motifs in a murine peritonitis model by their binding to highly expressed toll-like receptor-9 on liver NKT cells. *J Hepatol* 45:836-843.

Whitehouse, L.W., Paul, C.J., and Thomas, B.H. 1976. Effect of acetylsalicylic acid on a toxic dose of acetaminophen in the mouse. *Toxicol Appl Pharmacol* 38:571-582.

De Vries, J., De Jong, J., Lock, F.M., Van Bree, L., Mullink, H., and Veldhuizen, R.W. 1984. Protection against paracetamol-induced hepatotoxicity by acetylsalicylic acid in rats. *Toxicology* 30:297-304.

Kuida, K., Lippke, J.A., Ku, G., Harding, M.W., Livingston, D.J., Su, M.S., and Flavell, R.A. 1995. Altered cytokine export and apoptosis in mice deficient in interleukin-1 beta converting enzyme. *Science* 267:2000-2003.

Sutterwala, F.S., Ogura, Y., Szczepanik, M., Lara-Tejero, M., Lichtenberger, G.S., Grant, E.P., Bertin, J., Coyle, A.J., Galan, J.E., Askenase, P.W., et al. 2006. Critical role for NALP3/CIAS1/Cryopyrin in innate and adaptive immunity through its regulation of caspase-1. *Immunity* 24:317-327.

Schmassmann, A., Zoidl, G., Peskar, B.M., Waser, B., Schmassmann-Suhijar, D., Gebbers, J.O., and Reubi, J.C. 2006. Role of the different isoforms of cyclooxygenase and nitric oxide synthase during gastric ulcer healing in cyclooxygenase-1 and -2 knockout mice. *Am J Physiol Gastrointest Liver Physiol* 290:G747-756.

Loidl-Stahlhofen, A, et al. Solid-Supported Biomolecules on Modified Silica Surfaces—A Tool for Fast Physicochemical Characteerization and High-Throuphput Screening. Advanced Materials, 6pp, Nov. 23, 2001.

\* cited by examiner

Innate Immune Activation

COMPOSITIONS AND METHODS FOR REDUCING HEPATOTOXICITY ASSOCIATED WITH DRUG ADMINISTRATION

RELATED APPLICATIONS

The present application claims the benefit of priority of U.S. provisional application Ser. No. 60/999,413, filed Oct. 18, 2007, entitled "Protection From Acute and Chronic Liver Injury by Therapeutic Doses of Aspirin", the entire contents of said patent application being incorporated by reference herein.

This application is a U.S. National Stage of International Application No. PCT/US2008/011945 filed 20 Oct. 2010 and claims the benefit under 35 U.S.C. §119(e) of U.S. Provisional Patent Application No. 60/999,413 filed 18 Oct. 2007.

GOVERNMENT SUPPORT

This invention was supported by grants from the National Institutes of Health, grant numbers NIH KO8 AI065517, NIH R01DK076674-01A2 and NIH T32 DK7356. The government retains rights in this invention.

FIELD OF THE INVENTION

The present invention relates to the discovery that acetylsalicylic acid (ASA or aspirin), salicylic acid (SA) and related salicylate esters and their pharmaceutically acceptable salts, when coadministered in effective amounts with a drug or other bioactive agent which typically (in the absence of the salicylate compound) produces significant hepatotoxicity as a secondary indication, will substantially reduce or even eliminate such hepatotoxicity. Favorable therapeutic intervention results from the use of the present invention having the effect of reducing hepatotoxicity associated with the administration of certain drugs and other bioactive agents and in certain instances of allowing the administration of higher doses of a compound which, without the coadministration, would produce hepatotoxicity which limits or even negates the therapeutic value of the compound.

Compositions comprising a hepatotoxicity reducing effective amount of ASA and/or SA or related agents as described in greater detail herein, in combination with at least one drug or other bioactive agent which, in the absence of ASA or SA, produces substantial toxicity are an aspect of the present invention. Methods of using ASA and/or SA or related compounds to reduce hepatotoxicity associated with drug therapy, represents an additional aspect of the present invention. The present invention results in a patient being protected from acute and chronic liver toxicity associated with the administration of hepatotoxic bioactive agents.

BACKGROUND OF THE INVENTION

Acetaminophen (APAP) hepatotoxicity is the most common cause of death due to acute liver failure in the developed world, and is increasingly recognized as a significant public health problem (1, 2). The initial event in APAP induced hepatotoxicity is a toxic-metabolic injury leading to hepatocyte death by necrosis and apoptosis. This results in secondary activation of the innate immune response involving up-regulation of inflammatory cytokines with activation of NK, NKT cells and neutrophils, which significantly contributes to hepatotoxicity and mortality (3, 4). The molecular pathways for innate immune activation after hepatocyte death are of great interest as they are likely a common pathway in sterile inflammation.

IL-1β is a very potent pro-inflammatory cytokine, and IL-1β levels are known to be increased during APAP hepatotoxicity (5, 6). In addition signaling through the IL-1 receptor (IL-1R) was recently shown to be important in APAP induced hepatotoxicity (7). The mechanisms by which cellular death results in up-regulation of IL-1β and activation of the sterile inflammatory response are not known. In contrast to sterile inflammation there is extensive data on IL-1β up-regulation by a variety of pathogens. Activation of Toll-like receptors (TLRs) by pathogen-associated molecular patterns (PAMPs) results in up-regulation of pro-IL-1β via a MyD88, NF-kB pathway. Analogous to other potent inflammatory steps, production of IL-1β requires a second signal resulting in caspase-1 mediated cleavage of pro-IL-1β to release the active molecule (8-10).

Our approach was to try to identify the two signals which were responsible for IL-1β production in APAP hepatotoxicity. TLR9 was of interest to us as a candidate molecule responsible for the first signal in sterile inflammation because in addition to being activated by bacterial DNA rich in unmethylated CpG motifs it can also be activated by DNA from mammalian cells (11) (12). When mammalian cells undergo apoptosis genomic DNA is modified by the caspase-activated DNAase (CAD)-mediated cleavage, and also aberrant methylation and oxidative damage (13-15). These apoptosis mediated changes increase the ability of mammalian DNA to activate TLR9 (16).

The activity of caspase-1 is regulated by a cytosolic protein complex called the inflammasome consisting of a NALP family member, the adaptor protein ASC and caspase-1 (17). A variety of molecules can result in activation of NALP pathways. These include molecules from dying mammalian cells causing activation of the inflammasome via NALP3, and molecules from gram negative organisms causing activation via IPAF (17). The NALP3 inflammasome was of interest to us as a candidate molecule responsible for providing the second signal required for IL-1β activity in APAP hepatotoxicity, and this was tested using mice deficient in caspase-1, ASC, or NALP3. We further aimed to identify clinically applicable strategies for down-regulating the caspase-1 inflammasome pathway, and test if they provide protection from APAP induced hepatotoxicity.

BRIEF DESCRIPTION OF THE INVENTION

Figure 1:
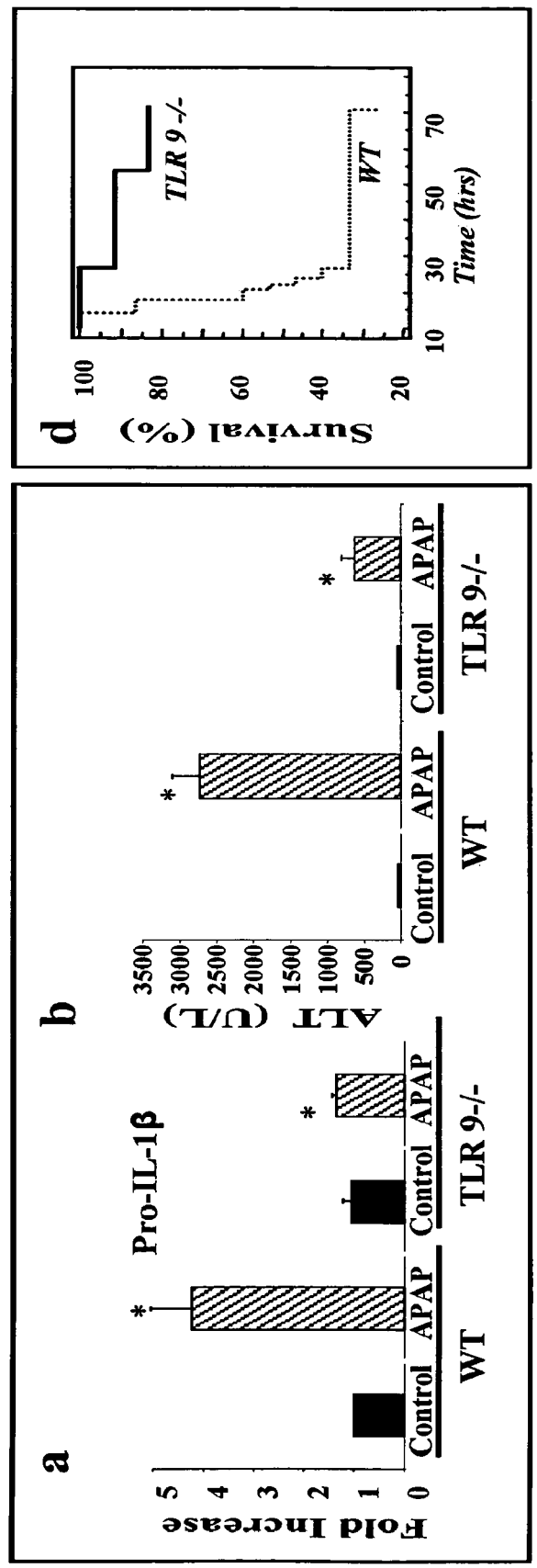
FIG. 1 shows that APAP-mediated hepatotoxicity is dependent on TLR9. (a) Increase in total liver pro-IL-1β transcript in wild-type mice twelve hours after APAP (500 mg/kg), which is significantly lower in TLR9−/− mice compared with wild-type (*P<0.01). (b) Significantly lower serum transaminases in TLR9−/− mice 12 hours after a single toxic dose of APAP, compared to wild-type (*P<0.01). (c) Less liver hemorrhage and necro-inflamation in TLR9−/− mice 12 hrs after APAP, compared with wild-type (H&E staining X20). (d) Kaplan-Mayer survival curves for wild-type and TLR9−/− mice over 72 hours after a single toxic dose of APAP (wild-type n=15, TLR9−/− n=17 P<0.04).
Figure 1:
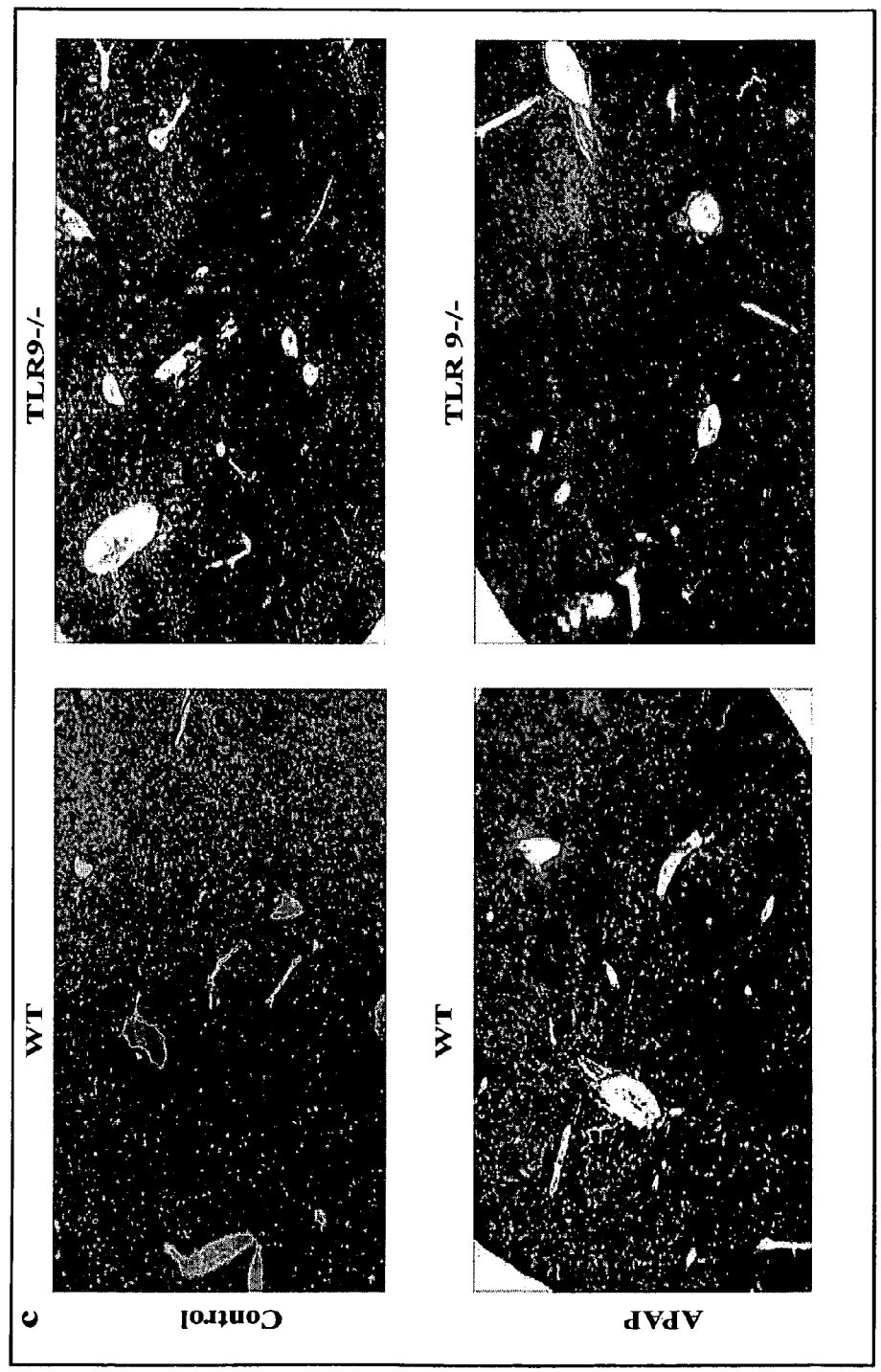

The present invention relates to the discovery that a salicylate compound according to the structure:

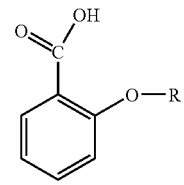

Where R is H or a $C_2$-$C_{10}$ acyl group (preferably H or an acetyl group), or a pharmaceutically acceptable salt thereof, may be used in combination with a bioactive agent which produces significant hepatotoxicity ("a hepatotoxicity inducing bioactive agent") in the absence of said salicylate compound to substantially reduce said hepatotoxicity. In preferred aspects of the invention, the salicylate compound is acetylsalicylic acid (aspirin, R=$C_2$ acyl or acetyl group) or a pharmaceutically acceptable salt thereof.

Thus, in one aspect, the present invention relates to pharmaceutical compositions which comprise an effective amount of a salicylate compound as set forth above, in combination with at least one bioactive agent which produces hepatotoxicity as a side effect, optionally in combination with a pharmaceutically acceptable carrier, additive or excipient. In certain aspects, the pharmaceutical composition includes a high dose effective amount of a bioactive agent in combination with the salicylate.

In another aspect, the present invention relates to a method for reducing hepatotoxicity secondary to the administration of bioactive agent which produces hepatotoxicity as a secondary or side effect, the method comprising coadministering an effective amount of at least one salicylate compound as described above in combination with said bioactive.

The present method is applicable and adaptable to a large number of hepatotoxicity inducing bioactive agents which produce hepatotoxicity and limit their usefulness because of that hepatotoxicity. The present invention may be used to increase the effectiveness of such bioactive agents (for example by increasing an agent's therapeutic index and/or increasing the dose which may be administered to a patient). Pursuant to the present invention, in some cases, bioactive agents which have, heretofore, been considered of limited utility as clinically relevant therapies because of significant hepatotoxicity associated with the administration of these agents are now clinically relevant, an important factor in enhancing the armamentarium against a number of disease states and conditions, especially including HIV infections, among others.

DETAILED DESCRIPTION OF THE INVENTION

The following terms shall be used to describe the present invention. In instances where a term is not specifically defined herein, the term shall be accorded its meaning, within the context of its use, as understood by those of ordinary skill in the art.

The term "compound" shall mean any specific compound which is disclosed within this specification and typically means a salicylate, salicylate ester or a pharmaceutically acceptable salt thereof, or a bioactive agent, including pharmaceutically acceptable salts thereof, generally a drug, in amounts effective to produce an intended physiological effect, but which also causes significant hepatotoxicity to a patient as a side or secondary effect of administering the drug to the patient. Pharmaceutically acceptable salts are also compounds for use in the present invention.

The term "effective" when used in context, shall mean any amount of a compound or component which is used to produce an intended result within the context of its use. In the case of bioactive agents according to the present invention, the term effective generally refers to a therapeutically effective amount of compound which will produce an intended physiological effect associated with that agent, and may include such activity as antimicrobial activity including antiviral, antibacterial, antifungal activity, etc. antimicrobial activity such as antiviral activity, antifungal activity, antibacterial activity, especially including or other pharmacological activity, including the treatment of diabetes, etc. In the case of salicylates, which are used in compositions according to the present invention to eliminate or reduce hepatotoxicity associated with the administration of a bioactive agent as otherwise described herein, an effective amount of salicylate is that amount which significantly decreases hepatotoxicity associated with the administration of the bioactive agent.

In preferred aspects of the invention, the amount of salicylate which is administered to a patient or subject to reduce the hepatotoxicity of the coadministered bioactive agent is an effective amount falling within the range from about 0.01 mg/kg to about 25 mg/kg, about 0.1 mg/kg to about 20 mg/kg, about 0.5 mg/kg to about 15 mg/kg, about 1.0 mg/kg to about 12.5 mg/kg, about 1.5 mg/kg to about 10 mg/kg, about 2.5 mg/kg to about 7.5 mg/kg, about 3.0 mg/kg to about 5 mg/kg, about 4 mg/kg to about 4.5 mg/kg. One of ordinary skill in the art may adjust the amount of salicylate coadministered with a bioactive agent to influence and reduce the hepatotoxicity of the coadminstered bioactive agent.

The bioactive agent which is administered is that amount effective to produce an intended therapeutic result and may vary widely. The amount of bioactive agent used in the instant invention to be combined with the salicylate compound and carrier materials to produce a single dosage form will vary depending upon the host treated, the particular mode of administration, the level of hepatotoxicity produced, etc. Preferably, the compositions should be formulated so that a therapeutically effective dosage of between about 0.1 µg/kg and 25 mg/kg, about 0.50 µg/kg and 20 mg/kg, about 1 µg/kg and 20 mg/kg about 5 µg/kg to about 15 mg/kg, about 500 µg/kg to about 10 mg/kg patient/day of the compound can be administered to a patient receiving these compositions.

In preferred aspects of the invention, the use of an effective amount of a salicylate as otherwise described herein, reduces the hepatotoxicity of a bioactive agent which produces hepatotoxicity in the absence of salicylate at least about 5-10%, at least about 20%, at least about 30%, at least about 40%, at least about 50%, at least about 60%, at least about 70%, at least about 80%, at least about 90%, at least about 95%, at least about 97%, at least about 99%, at least about 99.5% and at least about 100% (i.e., no appreciable hepatotoxicity can be detected in the patient or subject).

The term "high dose effective amount" is used through the specification to describe an amount of a bioactive agent which may be used in a composition according to the present invention which is above the typical dose ("elevated dose") which may be safely administered to a patient or subject in the absence of a hepatotoxicity reducing salicylate compound as otherwise described herein. A high dose effective amount is a dose of bioactive agent which would normally produce unacceptably high hepatotoxicity (elevated ALT, ALP or bilirubin) as otherwise described herein and would not be administered for that reason, but because of its coadministration with a salicylate (especially aspirin) and reduction in hepatotoxicity, may be administered at a higher dose due to a higher or increased therapeutic index. In preferred aspects a high dose effective amount is at least about 10% higher, 15% higher, 20% higher, 25% higher, 30% higher, 35% higher, 40% higher, 50% higher, 75% higher and 100% or more higher on a weight basis than the highest recommended dosage of a bioactive agent which induces hepatotoxicity in the absence of a salicylate as otherwise described herein.

The terms "bioactive agent" and "a hepatotoxicity inducing bioactive agent" are used synonymously in context to describe compounds which often produce hepatotoxicity in patients administered such agents. Bioactive agents as described herein produce significant hepatotoxicity in the absence of a salicylate compound as otherwise described herein which substantially reduces said hepatotoxicity. Bioactive agents which are used in the present invention (in combination pharmaceutical compositions) or affected by the methods of the present invention include both clinically relevant bioactive agents as well as bioactive agents which have had difficulty with regulatory approval and clinical use given the propensity to produce hepatotoxicity in patients.

Examples of bioactive agents which are used or affected by the present invention include virtually any compound which produces hepatotoxicity in a patient and includes, for example, anaesthetic agents, antiviral agents, anti-retroviral agents (nucleoside reverse transcriptase inhibitors and non-nucleoside reverse transcriptase inhibitors), especially anti-HIV agents, anticancer agents, organ transplant drugs (cyclosporin, tacrolimus, OKT3), antimicrobial agents (anti-TB, anti-fungal, antibiotics), anti-diabetes drugs, vitamin A derivatives, steroidal agents, especially including oral contraceptives, anabolic steroids, androgens, non-steroidal anti-inflammatory agents, anti-depressants (especially tricyclic antidepressants) glucocorticoids, natural products and herbal and alternative remedies, especially including St. John's wort.

Anti-TB Drugs:
  Isoniazid
  Ethambutol
  Pyrazinamide
  Ethionamide
Anti-fungal Drugs
  Diflucan
  Terbinafine
  Itraconazole
  Ketoconazole
  Voriconazole
  Posaconazole
Anti-Diabetes Drugs
  Rosiglitazone
  Pioglitazone
Vitamin A Derivatives
  Acitretin
  Isotretinoin
Anti-viral Drugs
  Indinavir
  Didanosine
  Emtricitabine
  Squinavir
  Raltegravir
  Ritonavir
  Lopinavir
  Lamivudine
  Delavirdine
  Zidovudine
  Atazanavir
  Maraviroc
  Efavirenz
  Nelfinavir
  Tenofovir
  Stavudine
  Abacavir
  Tipranavir
  Darunavir
  Festinavir
  Combivir (lamivudine/zidovudine)
  Epzicom (abacavir/lamivudine)
  Kaletra (lopinavir/ritonavir)
  Trizivir (abacavir/lamivudine/zidovudine)
  Truvada (emtricitabine/tenofovir)
  Atripla (efavirenz/emtricitabine/tenofovir)
Statins
  lovastatin
  pravastatin
  simvastatin
  atorvastatin
  amlodipine/atorvastatin (Caduet)
  rosuvastatin
  fluvastatin
  fluvastatin ER
  niacin/simvastatin (Simcor)
Non-statin Cholesterol Lowering Medications
  fenofibrate
  ezetimibe
  gemfibrozil
Non-Steroidal Anti-Inflammatory Drugs (NSAIDs)
  ibuprofen
  ibuprofen/oxycodone
  diclofenac
  diflunisal
  etodolac
  fenoprofen
  flurbiprofen
  indomethacin
  ketoprofen
  mecrofenamate
  nabumetone
  naproxen
  naproxen sodium
  oxaprozin
  salsalate
  sulindac
  tolmetin
  ketorolac
  piroxicam
  meloxicam
  prevacid/naproxen
  celecoxib
  mefenamic acid
  sumatriptan/naproxen sodium The following represents a more comprehensive list of individual bioactive agents which can produce significant hepatotoxicity and are favorably influenced by the present invention:

Acebutolol, indomethacin, phenylbutazone, allopurinol, isoniazid, phenytoin, atenolol, ketoconazole, piroxicam, carbamazepine, labetalol, probenecid, cimetidine, maprotiline, pyrazinamide, dantrolene, metoprolol, quinidine, diclofenac, mianserin, quinine, quinidine, diltiazem, naproxen, ranitidine, enflurane, para-aminosalicylic acid, sulfonamide antibiotics, ethambutol, penicillins (penicillin, benzylpenicillin, phenoxymethylpenicillin, ampicillin, amoxicillin, dicloxacillin, flucloxacillin, nafcillin, cloxacillin, penicillamine, etc.) sulindac, ethionamide, phenelzine, tricyclic antidepressants (desipramine, imipramine), halothane, phenindione, valproic acid, ibuprofen, phenobarbital, verapamil, adrenocortical steroids, phenothiazines, antithyroid drugs, phenytoin, tetracyclines, valproic acid, methotrexate, actinomycin D, chlorpropamide, erythromycin, azathioprine, cyclophosphamide, benzodiazepines (flurazepam, diazepam, chlordiazepoxide), captopril, cyclosporine, flutamide, carbamazepine, danazol, glyburide, carbimazole, gold salts, cephalosporins, disopyramide, griseofulvin, enalapril, haloperidol, ketoconazole, norethandrolone, mercaptopurine, tamoxifen, methyltestosterone, testosterone, thiabendazole, nifedipine, tolbutamide, nitrofurantoin, phenothiazines, propoxyphene, verapamil, allopurinol, hydralazine, procainamide, carbamazepine, chlorpromazine, nitrofurantoin, diltiazem, tolbutamide, disopyramide, phenylbutazone, dantrolene, methyldopa, terbinafine (HCl), nicotinic acid, chlorpromazine/valproic acid (combination), thorotrast, danazol, labetolol, adriamycin, dacarbazine, thioquanine, vincristine, vitamin A (excess doses), carmustine, mitomycin, maprotiline, probenecid, piroxicam, diclofenac, enflurane, sulindac, phenindione, glyburide, haloperiodol, norethandolone, amiodarone, felbamate, fenofibrate, femfibrozil, fenofibrate and femfibrozil (combination), imatinib, leflunomide, nefazodone, niacin, aminosalicyclic acid/aminosalicylate sodium, capreomycin sulfate clofazimine, cycloserine, clopidogrel, kanamycin sulfate, rifabutin, rifampin, rifapentine, streptomycin sulfate, gatifloxacin, tacrine and riluzole (glutamate modulator), among others, including troglitazone, bromfenac, trovafloxacin, ebrotidine, nimesulide, nefazodone and ximelagatran.

The term "hepatotoxicity" or "drug induced hepatotoxicity" is used to describe hepatotoxicity (liver toxicity) which occurs as a consequence of chemical-driven liver damage. The liver plays a central role in transforming and clearing chemicals and is susceptible to the toxicity from these agents. Certain medicinal agents when taken in overdoses and sometimes even when introduced within therapeutic ranges may injure the organ. Other chemical agents such as those used in laboratories and industries, natural chemicals (e.g. microcystins) and herbal remedies can also induce hepatotoxicity. Chemicals that cause liver injury are called hepatotoxins. More than 900 drugs have been implicated in causing liver injury and it is the most common reason for a drug to be withdrawn from the market. Chemicals often cause subclinical injury to liver which manifests only as abnormal liver enzyme tests. Drug induced liver injury is responsible for 5% of all hospital admissions and 50% of all acute liver failures.

Drugs and other chemicals may produce a wide variety of clinical and pathological hepatic injury. Biochemical markers (i.e. alanine transferase, alkaline phosphatase and bilirubin) are often used to indicate liver damage. Liver injury is defined as an increase in either (a) ALT level more than three times of upper limit of normal (ULN), (b) ALP level more than twice ULN, or (c) total bilirubin level more than twice ULN when associated with increased ALT or ALP. Liver damage is further characterized into hepatocellular (predominantly initial alanine transferase elevation) and cholestatic (initial alkaline phosphatase rise) types. However these are not mutually exclusive and mixed type of injuries are often encountered.

In the present invention, the inclusion of a salicylate compound as otherwise described herein produces a substantial reduction (at least about 10% reduction, at least about 20% reduction, at least about 25% reduction, at least about 30% reduction, at least about 35% reduction, at least about 40% reduction, at least about 45% reduction, at least about 50% reduction, at least about 60% reduction, at least about 65% reduction, at least about 75% reduction, at least about 85% reduction, at least about 90% reduction or more) of hepatotoxicity such that at least one of alanine transferase (ALT) activity, alkaline phosphatase (ALP) activity and total bilirubin level, preferably at least ALT and ALP and preferably ALT, ALP and bilirubin levels are all reduced by levels as described above.

Specific histo-pathological patterns of liver injury from drug induced damage are discussed below.

Zonal Necrosis

This is the most common type of drug induced liver cell necrosis where the injury is largely confined to a particular zone of the liver lobule. It may manifest as very high level of ALT and severe disturbance of liver function leading to acute liver failure.

Causes:
Acetaminophen (Tylenol), carbon tetrachloride
Hepatitis

In this pattern hepatocellular necrosis is associated with infiltration of inflammatory cells. There can be three types of drug induced hepatitis. (A) viral hepatitis type picture is the commonest, where histological features are similar to acute viral hepatitis. (B) in the focal or non specific hepatitis scattered foci of cell necrosis may accompany lymphocytic infiltrate. (C) chronic hepatitis type is very similar to autoimmune hepatitis clinically, serologically as well as histologically.

Causes:
(a) Viral hepatitis like: Halothane, Isoniazid, Phenytoin
(b) Focal hepatitis: paraaminobenzoic acid, oral contraceptives, aspirin
(c) Chronic hepatitis: Methyldopa, Diclofenac
Cholestasis Liver injury leads to impairment of bile flow and clinical picture is predominated by itching and jaundice. Histology may show inflammation (cholestatic hepatitis) or it can be bland without any parenchymal inflammation. In rare occasions it can produce features similar to primary biliary cirrhosis due to progressive destruction of small bile ducts (Vanishing duct syndrome).

Causes:
(a) Bland: Oral contraceptive pills, anabolic steroid, Androgens
(b) Inflammatory: Allopurinol, Co-amoxiclav, Carbamazepine
(c) Ductal: Chlorpromazine, flucloxacillin
Steatosis Hepatotoxicity may manifest as triglyceride accumulation which leads to either small droplet (microvesicular) or large droplet (macrovesicular) fatty liver. There is a separate type of steatosis where phospholipid accumulation leads to a pattern similar to the diseases with inherited phospholipid metabolism defects (e.g. Tay-Sachs disease)

Causes:
(a) Microvesicular: Ketoprofen, Tetracycline
(b) Macrovesicular: Acetamenophen, methotrexate
(c) Phospholipidosis: Amiodarone, Total parenteral nutrition
Granuloma Drug induced hepatic granulomas are usually associated with granulomas in other tissues and patients typically have features of systemic vasculitis and hypersensitivity. More than 50 drugs have been implicated.

Causes:
Allopurinol, Phenytoin, Isoniazid, Quinine, Penicillin, Quinidine
Vascular Lesions Vascular lesions result from injury to the vascular endothelium.

Causes:
Venoocclusive disease: Chemotherapeutic agents, bush tea
Peliosis hepatis: anabolic steroid
Hepatic vein thrombosis: Oral contraceptives The term "pharmaceutically acceptable salt" is used throughout the specification to describe a salt form of one or more of the compounds described herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids, especially salts of carboxylic acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids in compositions according to the present invention. The term "salt" shall mean any salt consistent with the use of the compounds according to the present invention. As used herein, the term "salt" shall mean a pharmaceutically acceptable salt, consistent with the use of the compounds as pharmaceutical agents.

The term "therapeutic index" (also known as therapeutic ratio), is a comparison of the amount of a therapeutic agent that causes the therapeutic effect to the amount that causes toxic effects, as used in the present invention, hepatotoxicity. Quantitatively, it is the ratio given by the dose causing hepatotoxicity divided by the therapeutic dose. A measure of therapeutic index used herein is the hepatotoxic dose of a drug for 50% of the population ($TD_{50}$) divided by the minimum effective dose for 50% of the population ($ED_{50}$). A high therapeutic index is preferable to a low one: this corresponds to a situation in which one would have to take a much higher amount of a drug to do harm than the amount taken to provide a therapeutic effect.

In the past, a drug with a narrow therapeutic range (i.e. with little difference between hepatotoxic and therapeutic doses) may have its dosage adjusted according to measurements of the actual blood levels achieved in the person taking it. This may be achieved through therapeutic drug monitoring (TDM) protocols. However, using the present invention (an effective amount of a salicylate, especially aspirin, as otherwise described herein), the therapeutic index of a bioactive agent administered in the absence of a salicylate, especially aspiring, as otherwise described herein, may be increased appreciably, i.e., at least about 10%, at least about 15%, at least about 20%, at least about 25%, at least about 30%, at least about 35%, at least 40%, at least 45%, at least 50%, at least 60%, at least 75%, at least 90%, at least 95%, at least about 100%, at least about 150% (at least 1.5 times the therapeutic index without coadministration of a salicylate as described herein), at least about 200%, at least about 300%, at least about 500%, at least about 1000% (at least 10 times the original therapeutic index).

The term "coadministration" or "combination therapy" is used to describe a therapy in which a salicylate which reduces or ameliorates hepatotoxicity of another agent is combined with a bioactive agent as otherwise described herein. The bioactive agent used in the present invention may be used to treat a wide range of disease states and/or conditions and may exhibit a wide variety of pharmacological or physiological effects. Although the term coadministration preferably includes the administration of two compounds, at least one salicylate as otherwise described herein as well as a bioactive to the patient at the same time, it is not necessary that the compounds be administered to the patient at the same time, although effective amounts of the individual compounds will be present in the patient at the same time. Compounds according to the present invention are preferably coadministered in a single composition, preferably which is at least sustained or controlled release with respect to the hepatotoxicity reducing salicylate compound which is used. In other instances, both the hepatotoxicity reducing salicylate compound and the bioactive agent are both formulated for sustained or controlled release administration.

The term "sustained release" or "controlled release" is used to describe administration of a salicylate and/or a bioactive agent as otherwise described herein over a sustained or controlled period of time, oftentimes for periods of at least about 4 hours, at least about 6 hours, at least about 8 hours, at least about 10 hours, at least about 12 hours, at least about 16 hours, at least about 20 hours, at least about 24 hours, at least about 2 days up to a week or more. In certain embodiments which are delivered from transdermal patches, release may occur over several weeks or more. The release rate for the salicylate according to the present invention may differ from the release rate of the bioactive agent. Sustained or controlled release compositions according to the present invention contrast with delayed release, immediate release or "bolus" release administration of compounds or delayed release compounds, which represent alternative embodiments of the present invention. Immediate release compositions are those which release agents substantially immediately as a bolus dose. Delayed release compositions are those which release agents in a somewhat slower manner than an immediate release composition, but which do not release agents in a controlled or sustained release manner. See, for example, fda.gov/cder/guidance/4964dft.htm at fda.gov/cder, among other sources.

In order to provide sustained or controlled release compositions hereunder, well known techniques for influencing the release rate of compositions may be used. Conventional formulation techniques may be used in order to provide sustained or controlled release compositions according to the present invention. Sustained or controlled release compositions according to the present invention may be provided wherein salicylate and bioactive agent are delivered from the same sustained or controlled release matrix in a tablet, capsule, transdermal patch, topical creams or the like, or alternatively, each of the salicylate compound and the bioactive agent, although being delivered from the same capsule, tablet, patch, cream, etc., may be delivered from different matrices which release compound therefrom at differing rates in order to provide effective concentrations in the blood, plasma and/or serum of the patient.

Sustained or controlled release formulations which may be used to formulate the present compositions include those which are disclosed in inter alia, U.S. Pat. Nos. 4,508,702; 4,520,009; 4,970,081; 4,988,679; 4,753,801; 4,755,387; 4,629,621; 4,308,251; 4,302,440; 5,004,613; 4,460,368; 4,555,399; 4,316,884; 4,025,613; 4,829,523; and 4,867,984, relevant portions of which patents are incorporated by reference herein.

Pursuant to the present invention, the inclusion of a salicylate compound as otherwise described herein produces a substantial reduction (at least about 5-10% reduction, at least about 20% reduction, at least about 25% reduction, at least about 30% reduction, at least about 35% reduction, at least about 40% reduction, at least about 45% reduction, at least about 50% reduction, at least about 60% reduction, at least about 65% reduction, at least about 75% reduction, at least about 85% reduction, at least about 90% reduction) of hepatotoxicity caused by a bioactive agent as otherwise described herein such that at least one of alanine transferase (ALT) activity, alkaline phosphatase (ALP) activity and total bilirubin level, preferably at least ALT and ALP and preferably ALT, ALP and bilirubin levels are all reduced by levels as described above.

Compounds according to the present invention may be used in pharmaceutical compositions having biological/pharmacological activity for the treatment of, for example, microbial infections, including viral infections such as HIV infections, Mycobacterial infections, especially *Mycobacterium tuberculosis* (tuberculosis) infections, fungal infections, including *Candida* infections, among numerous others, for the treatment of diabetes and for the treatment of skin conditions such as acne, as well as numerous other disease states and/or conditions as otherwise described herein. Virtually any bioactive agent which produces hepatotoxicity may be utilized in the present invention in combination with an effective amount of a salicylate compound as otherwise described herein.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously. Preferred routes of administration include oral administration, sublingual or buccal administration and pulmonary administration (by inhaler/inhalation spray).

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions, preferably as sustained release compositions, at least for the salicylate administered. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application. Suitable topical formulations are readily prepared for each of these areas or organs.

Topical application also can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In preferred aspects of the invention, the amount of salicylate which is administered to a patient or subject to reduce the hepatotoxicity of the coadministered bioactive agent is an effective amount falling within the range from about 0.01 mg/kg to about 25 mg/kg, about 0.1 mg/kg to about 20 mg/kg, about 0.5 mg/kg to about 15 mg/kg, about 1.0 mg/kg to about 12.5 mg/kg, about 1.5 mg/kg to about 10 mg/kg, about 2.5 mg/kg to about 7.5 mg/kg, about 3.0 mg/kg to about 5 mg/kg, about 4 mg/kg to about 4.5 mg/kg. One of ordinary skill in the art may adjust the amount of salicylate coadministered with a bioactive agent to influence and reduce the hepatotoxicity of the coadminstered bioactive agent. The amount of salicylate used in the instant invention to be combined with a bioactive agent and carrier materials to produce a single dosage form will vary depending upon the host treated, the particular mode of administration, the therapeutic target, the level of hepatotoxicity produced by a bioactive agent, etc.

The amount of bioactive agent used in the instant invention to be combined with the salicylate compound and carrier materials to produce a single dosage form will vary depending upon the host treated, the particular mode of administration, etc. Preferably, the compositions should be formulated so that a therapeutically effective dosage of between about 0.1 μg/kg and 25 mg/kg, about 0.50 μg/kg and 20 mg/kg, about 1 μg/kg and 20 mg/kg about 5 μg/kg to about 15 mg/kg, about 500 μg/kg to about 10 mg/kg patient/day of the compound can be administered to a patient receiving these compositions.

Preferably, pharmaceutical compositions in dosage form according to the present invention comprise a therapeutically effective amount of at least about 5 μg of bioactive agent, at least about 25 μg of bioactive agent, at least about 100 μg of bioactive agent, at least about 500 μg of bioactive agent, at least about 1 mg of bioactive agent, at least about 10 mg of bioactive agent, at least about 15 mg of bioactive agent, at least about 25 mg of bioactive agent, at least 50 mg of bioactive agent, at least 60 mg of bioactive agent, at least about 75 mg of bioactive agent, at least about 100 mg of bioactive agent, at least 150 mg of bioactive agent, at least 200 mg of bioactive agent, about 250 mg of bioactive agent, about 300 mg of bioactive agent, about 350 mg of bioactive agent, about 400 mg of bioactive agent, about 500 mg of bioactive agent, about 750 mg of bioactive agent, about 1 g (1000 mg) of bioactive agent, alone or in combination with a therapeutically effective amount of at least one additional bioactive agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated. The amount of salicylate compound which is included in a pharmaceutical composition or otherwise administered to a patient or subject will vary with the ability of the bioactive agent to induce heptatoxicity.

Coadministration of the active compounds may range from continuous (intravenous drip) to one or more oral or inhalation (intratracheal) administrations per day (for example, a single sustained or controlled release dose, B.I.D. or Q.I.D.) and may include oral, pulmonary, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance, in addition to the fact that oral dosage forms lend themselves more easily to sustained or controlled release administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In preferred aspects, the present invention also relates to pharmaceutical compositions in oral dosage form comprising effective amounts of aspirin in combination with effective amounts of a bioactive agent according to the present invention, optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

The pharmaceutical compositions of the invention are safe and effective for use in the therapeutic methods according to the present invention. Although the dosage of the individual components of the composition of the invention may vary depending on the type of active substance administered and optional additional agents as well as the nature (size, weight, etc.) of the subject to be diagnosed, the composition is administered in an amount effective for allowing the pharmacologically active substance to exhibit its inherent therapeutic effect, with reduced hepatotoxicity associated with the coadministration of the salicylate as otherwise described herein. For example, the composition is preferably administered in sustained release oral, topical, sublinguial or buccal dosage forms, from once a day up to two (BID) or four times a day (QID). The form of the pharmaceutical composition of the invention such as a tablet, capsule, powder, solution, suspension etc. may be suitably selected according to the type of substance to be administered.

Not to be limited by way of mechanism, the present inventors have shown that hepatocyte death results in a sterile inflammatory response which amplifies the initial insult and increases liver injury. A clinically important example is acetaminophen induced liver injury in which there is initial toxic injury, followed by innate immune activation. Using mice deficient in TLR9 and the inflammasome components NALP3, ASC and caspase-1, the inventors have identified a non-redundant role for TLR9 and the NALP3 inflammasome in acetaminophen induced injury. There is an initial toxic injury resulting in hepatocyte death. DNA from the apoptotic hepatocytes subsequently activates TLR9, and provides the signal for pro-IL-1β and pro-IL-18 transcription. The NALP3 inflammasome provides the second signal for cleavage and activation of these cytokines by caspase-1. Liver sinusoidal endothelial cells express TLR9, up-regulate pro-IL-1β and pro-IL-18 in response to DNA from apoptotic hepatocytes, and demonstrate caspase-1 activation in vivo after acetaminophen injury. TLR9 antagonists and aspirin reduce mortality from acetaminophen hepatotoxicity. The protective effect of aspirin on acetaminophen-induced liver injury is not via inhibition of cox-1 or platelet degranulation, but rather by down regulation of pro-inflammatory cytokines. In summary we have identified a two signal requirement of TLR9 and inflammsome activation for full acetaminophen hepatotoxicity, and demonstrated novel therapeutic approaches to improve survival using a salicylate compound as otherwise described herein.

EXAMPLES

The following description of experiments conducted are presented to exemplify the present invention. They are by way of example only and are not to be taken the limit the invention in any way.

Materials and Methods

Animals.

C57BL/6 mice were purchased from commercial sources. NALP3−/−, IL-18−/− ASC−/−, IPAF−/− and TLR9−/− mice were backcrossed nine generations onto the C57BL/6 background. Caspase 1−/− mice were backcrossed 5-6 generations onto the C57BL/6 background. These mice have been described previously (39, 40). IL-1β was neutralized in by using the anti-IL-1β antibody from clone B122 (a gift of R. Schreiber, Washington University) at a dose of 0.2 mg/mouse iv twice a day for a total of 48 hours after giving APAP. Control mice received Armenian hamster isotype control antibody. For survival experiments animals were euthanized when they became moribund using criteria of lack of response to stimuli or lack of righting reflex. Animal protocols were approved by the Yale University animal care and use committee. [include references for IPAF−/− (M. Lara-Tejero et al. JEM 2006) and IL-18−/−. Need to add TLR9−/− and TLR3−/−]

Acetaminophen Induced Hepatotoxicity.

APAP (Sigma, Mo.) solution was made fresh for each experiment in PBS at 20 mg/ml and heated in a water bath to 55° C. to dissolve. APAP was dosed at 500 mg/kg and injected I.P after 15 hrs of starvation. Animals were euthanized by ketamine/xylazine injection at 12 hours for collection of serum, isolation of liver lymphocytes or collection of liver tissue for histology, or they were observed every four hours for 72 hours until they reached criteria for euthanasia (lack of response to stimuli or lack of righting reflex).

Aspirin/Clopidogrel/SC-560.

Aspirin (Sigma, Mo.) was made fresh for each experiment. For dosing prior to APAP it was dissolved in single deionized water at 60 mg/l and heated to 42° C. with rapid stirring to dissolve, then rapidly placed in an ice water bath to cool. Aspirin in water was given to the mice 60-72 hours prior to APAP injection. Assuming water consumption of 3-5 ml per day this dose would be equivalent to a 300-500 mg dose in an 80 kg adult human. For co-administration of APAP and aspirin, aspirin was gavaged at a dose of 6 mg/kg in a volume of 100 ul of water immediately after ip injection of APAP. Clopidogrel (Gilead Pharmaceuticals, CA.) was dissolved in PBS at 6 mg/ml and administered by gavage of 100 ul, 30 mg/kg, every 24 hours beginning 48 hours prior and ending 24 hours after APAP injection. Cox-1 inhibitor (SC-560). SC-560 (Cayman chemical, MI) was dissolved at 50 mg/ml in DMSO and further dissolved in PBS in order to gavage a dose of 5 mg/kg in 100 ul. It was administered twice per day beginning 60 hours prior to Tylenol and continued for 48 hours after APAP injection as previously established(41).

Uric Acid Peritonitis.

Peritonitis was induced with uric acid crystals as previously described by injecting 3 mg of MSU intraperitoneally per mouse (27). Three hours after injection peritoneal lavage was performed on mice euthanized by isoflurane inhalation. Neutrophil infiltration was evaluated by flow cytometry. The percent of Gr-1 (BD Pharmingen, CA) positive cells was multiplied by the total cell counts.

Liver Sinusoidal Endothelial Cell (LSEC) Isolation.

After in-situ pronase digestion the non-parenchymal cell suspension is centrifuged for 5 min at 100 g to remove most of the parenchymal cells. This process is repeated until no pellet is observed. The supernatant enriched in LSEC is centrifuged for 10 min at 350 g. The pellet is resuspended in PBS and centrifuged for 10 min at 350 g. The cells are resuspended in PBS and layered (3.3 ml) on the top of two-step percoll gradient (put the 5 ml of 50% percoll at the bottom and put the 6.6 ml of 25% percoll at the top). The gradients are centrifuged at 900 g for 20 min and the intermediate layer included LSEC is collected and cultured in the media (EGM™-2 MV—Microvascular Endothelial Cell Medium-2, CAMBREX, Charles City, Iowa).

ODN2088 and IRS 954 Injection.

TLR9 antagonist (ODN2088, 50 microg×2) or PBS, were injected ip into wild-type mice immediately after and at 6 hours after APAP injection and total mouse liver was obtained 12 hours after APAP injection for quantitative Q-PCR for IL-1β. IRS 954 (Dynavax Technologies) was injected ip at a dose of 150 mcg per mouse immediately after APAP and at 14 and 28 hrs.

Apoptotic DNA Portal Vein Injection.

DNA from healthy and apoptotic hepatocytes (200 microg) was isolated using Qiagen DNeasy Tissue Kit according to the manufacturers directions. Hepatocytes were cultured in 15 mm dishes, and when near confluent were exposed to 600 mJ of ultraviolet irradiation using a UV Stratalinker 1800 (Stratagene, La Jolla, Calif.). Cell apoptosis was evident 6 hours after irradiation via typical morphological changes. At this time, DNA was extracted and run on a standard eithidium bromide stained gel to confirm DNA degradation consistent with apoptosis. DNA was injected via the portal vein in wt and TLR9−/− mice. After 12 hrs total mouse liver was obtained for histology and Q-PCR for IL-1β and IL-18.

LSECs.

Primary mouse LSECs from the Wild-type and TLR9−/− mice were cultured in the presence of apoptotic DNA (50 μg/ml), apoptotic DNA+TLR9 antagonist (ODN2088; Invivogen, San Diego, Calif.). Twenty-four hours after culture, complementary DNA was prepared.

Quantitative Real-Time PCR.

Q-PCR was performed for IL-1β and IL-18 using commercial primer-probe sets (Applied Biosystems, Framingham, Mass.) and the Applied Biosystem 7500 real-time PCR system. Expression of glyceraldehyde 3-phosphate dehydrogenase was used to standardize the samples, and the results were expressed as a ratio compared with untreated HSCs. Quantitative Real-time PCR for mRNA expression of IL-18, IL-1β, TNF-α and IFN-γ. Total mouse liver was obtained 12 hours after APAP and cDNA was prepared. Quantitative real-time PCR (Q-PCR) was performed for IL-18 and IL-1β using commercial primer-probe sets (Applied Biosystems, Calif.) and the Applied Biosystem 7500 real time PCR system. Expression of GAPDH was used to standardize the samples, and the results were expressed as a ratio compared to control.

Western Blots.

Caspase 1 Western blots were carried out by standard protocols using cell lysate from $2 \times 10^5$ LSEC and anti-caspase-1 antibody (Santa Cruz Biotechnology, Calif.). ELISA for serum IL1-β was carried out by standard protocols.

Cell Line.

The human monocytic cell line THP1 was maintained in RPMI with 10% FBS. Stimulation with LPS (Sigma, Mo.) was performed by plating cells at $5 \times 10^5$ per 24 well, incubating overnight with aspirin or control media prior to adding LPS at 10 μg/ml for 8 hours.

Statistical Analysis.

Kaplan-Meier plots and statistical analysis were performed using MedCalc software version 9.2.0.1. Unpaired 1-tailed students T test was used to compare groups.

Results

Reduced Mortality and Liver Injury in TLR9−/− Mice in Response to APAP

To test if TLR9 has a role in the up-regulation of IL-1β we quantified pro-IL-1β transcripts in the livers of wild-type and TLR9-deficient mice twelve hours after a toxic dose of APAP (ip 500 mg/kg). There was a significant increase in pro-IL-1β transcripts in the livers of wild-type mice 12 hrs after APAP, which was markedly decreased in TLR9−/− mice (FIG. 1a). To establish that the reduction in pro-IL-1β expression was associated with decreased liver injury, we assayed serum alanine transaminase (ALT) and examined liver histology 12 hrs after APAP. In TLR9−/− mice serum ALT levels were significantly lower, and there was less hepatic hemorrhage and necro-inflammation (FIG. 1b-c). To test if the reduced pro-IL-1β expression and hepatotoxicity were associated with improved survival, wild-type and TLR9−/− mice were monitored over 72 hours after APAP (ip 500 mg/kg). There was dramatically reduced mortality in the TLR9−/− mice after APAP, compared to wild-type mice (wild-type n=15, TLR9−/− n=17 P<0.04) (FIG. 1d).

TLR Antagonists Reduce APAP Induced Liver Injury in Wild-Type Mice

Figure 2:
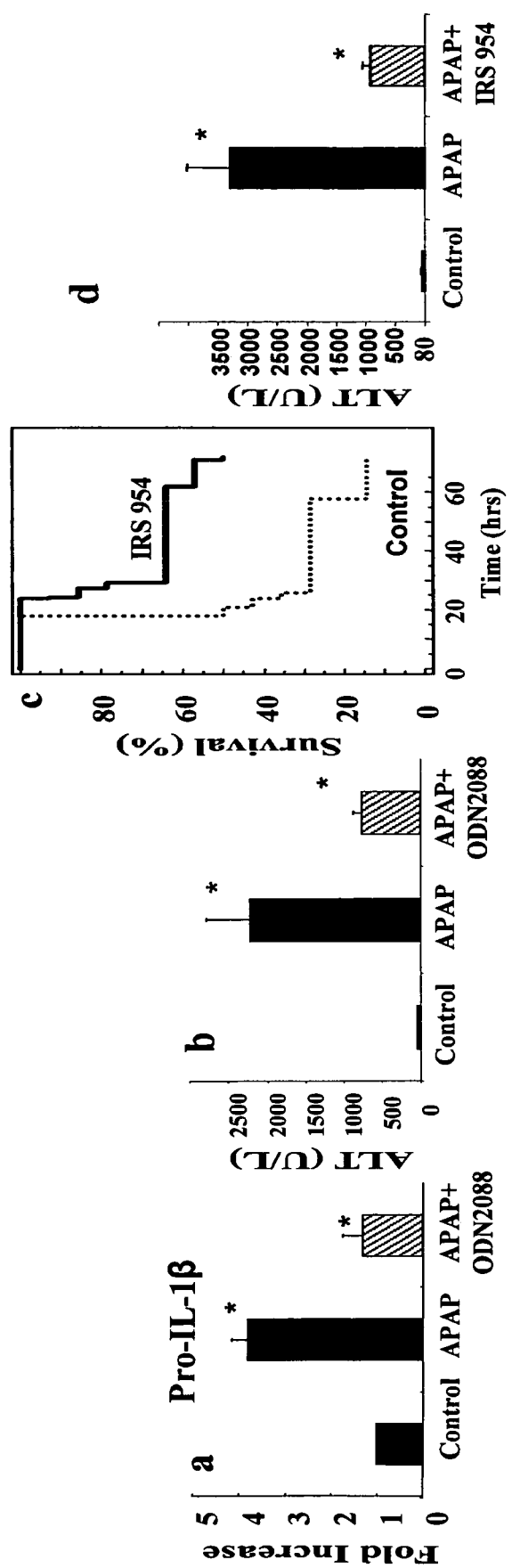
FIG. 2 shows the reduction in liver injury by TLR9 antagonist and induction of liver injury with apoptotic DNA. (a-b) Treatment of wild-type mice with the TLR9 antagonist ODN2088 significantly reduced APAP induced rise in liver pro-IL-1β transcript and serum transaminases (APAP compared to APAP+ODN2088 *P<0.01). (c-d) The TLR 7 and 9 antagonist IRS 954 significantly decreased mortality from APAP over 72 hours, and also reduced elevations in serum ALT at 12 hrs after APAP (control n=14, IRS 964 n=14 P<0.006) (APAP compared to APAP+ODN2088 *P<0.01). (e-g) Direct administration of DNA from apoptotic hepatocytes into the blood supplying the liver resulted in an increase in hepatic transcripts of pro-IL-1β and pro-IL-18 in wild-type mice, and serum transaminases. Both serum transaminases and pro-IL-1β and pro-IL-18 transcripts were lower after injection of DNA from healthy hepatocytes (healthy DNA compared to apoptotic DNA *p<0.01). (h-j) In control TLR9−/− mice there were no significant changes in serum transaminases, and hepatic transcripts of IL-1β and IL-18 after direct administration of DNA from apoptotic or healthy hepatocytes.
Figure 2:
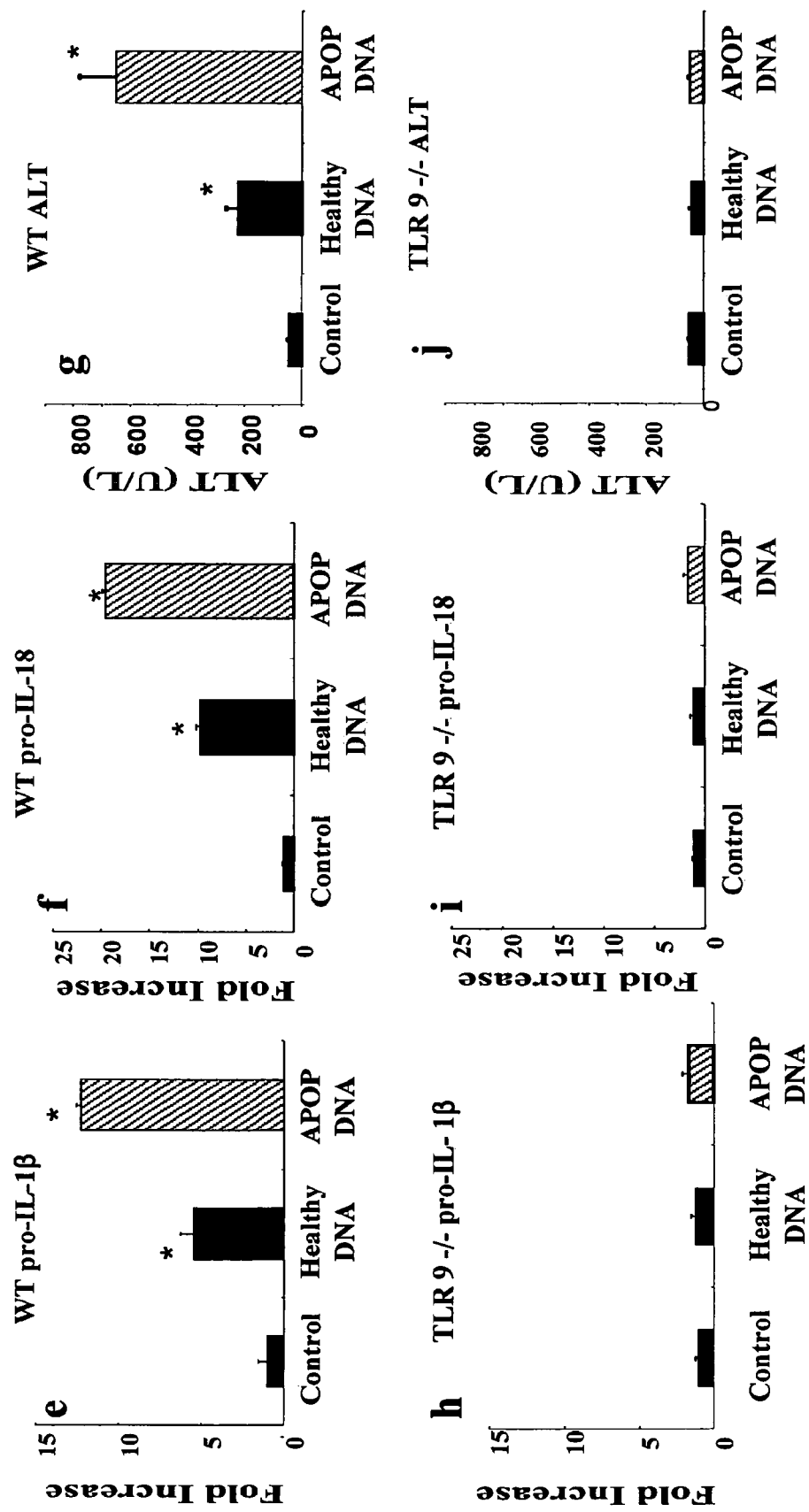

Having demonstrated reduced liver injury and improved survival in TLR9−/− mice we wanted to test if liver injury could be reduced in wild-type mice with the administration of a TLR9 antagonist. The TLR9 antagonist ODN2088 (50 microg×2) or PBS, were injected ip to wild-type mice immediately after, and at 6 hours after APAP injection, and serum and total mouse liver was obtained at 12 hours after APAP injection for quantitative Q-PCR and ALT assay. Injection of ODN2088 significantly reduced pro-IL-1β transcripts and serum ALT (FIG. 2a-b). We next wanted to demonstrate an improvement in survival from APAP hepatotoxicity using a TLR antagonist in clinical development. The immunoregulatory sequence 954 (IRS 954) can inhibit TLR9 and TLR 7, and has been shown to ameliorate disease in models of systemic lupus erythematosus (18, 19). We administered IRS 964 (150 mcg/mouse ip) immediately after a toxic dose APAP and at 14 and 28 hrs. Administration of IRS 964 resulted in a significant decrease in serum transaminases at 12 hrs and improved survival (FIG. 2c-d) (control n=14, IRS 964 n=14 P<0.006). This further confirms the importance of TLR9 in APAP hepatotoxicity, and also identifies a viable new therapeutic strategy which may be applicable to other diseases caused by a sterile inflammatory response.

DNA from Apoptotic Cells Up-Regulates Liver pro-IL-1β, pro-IL-18 in a TLR9 Dependent Manner To directly test if apoptotic DNA can upregulate pro-IL-1β and induce liver injury we injected DNA (200 microg/mouse) from healthy and apoptotic hepatocytes directly into the portal vein of wild-type mice and examined up-regulation of pro-IL-1β. Twelve hours after injection of DNA there was significant up-regulation of pro-IL-1β transcript and an increase in serum ALT levels (FIGS. 2e and 2g). Pro-IL-1β up-regulation and ALT elevations were significantly greater in response to DNA from apoptotic cells, as compared to healthy cells. IL-18 is important in many types of liver injury, and is also dependent on capsase-1 for cleavage and activation (20). In contrast to pro-IL-1β there is significant basal level of pro-IL-18 transcript in many cell types, but this can be up-regulated by viral infection and bacterial products (21, 22). Analogous to pro-IL-1β, there was significant up-regulation of pro-IL-18 in response to mammalian DNA and this was greater for DNA from apoptotic hepatocytes (FIG. 2f). To confirm that up-regulation of pro-IL-1β, pro-IL-18 and increase in serum ALT were due to actions of hepatocytes DNA via TLR9, the experiments were performed in parallel in TLR9−/− mice. There were no significant changes in either pro-IL-1β or pro-IL-18, and no increase in serum ALT (FIG. 2h-j).

DNA from Apoptotic Cells Up-Regulates pro-IL-1β and pro-IL-18 in Sinusoidal Endothelium in a TLR9 Dependent Manner Having demonstrated an important role for TLR9 in APAP and DNA induced liver injury the inventors were interested in identifying the liver cell type responding to TLR9. A number of cell types in the liver have the ability to respond to TLR9 including stellate cells and NK-T cells(23). The majority of TLR9 expression in the liver is however on sinusoidal endothelium, and we therefore focused on this cell type as a candidate for TLR9 activation and up-regulation of pro-IL-1β and pro-IL-18 (24). To initially test if classic non-immune cells such as endothelium are important in the up-regulation of pro-IL-1β and pro-IL-18 after APAP induced hepatotoxicity we gave a toxic dose of APAP to genetically altered mice lacking the genes of Rag 1 and common gamma chain (rag1−/−γ−/−), and compared them to wild-type mice. Rag1−/−γ−/− mice are lacking T, B, NK and NK-T cells and other lineages are reduced, and their livers still had significant up-regulation of pro-IL-1β and pro-IL-18 suggesting that non-immune cells have a significant role (FIG. 3a-b) (25).

Figure 3:
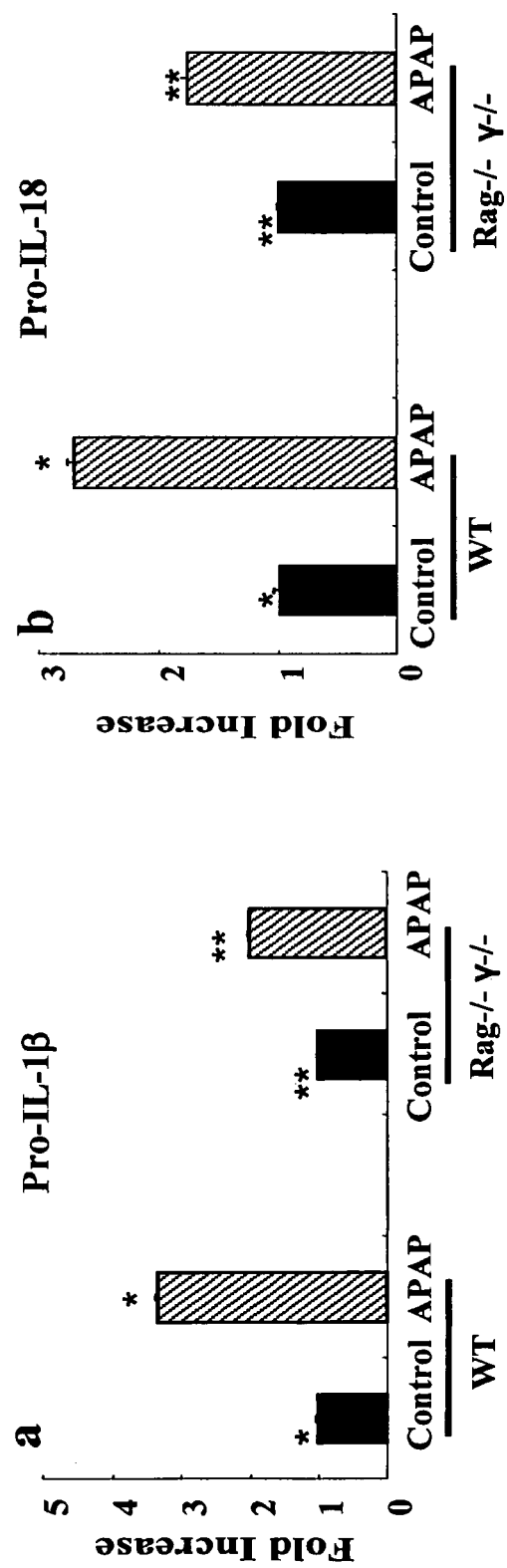
FIG. 3 shows that DNA from apoptotic hepatocytes increases pro-IL-1β and pro-IL-18 transcripts in primary liver endothelial cells and this is inhibited by TLR9 antagonist. (a-b) To determine if APAP induced up-regulation of pro-IL-1β and pro-IL-18 was dependent on immune cells we examined the livers of Rag 1, γ common chain double knockout mice which lack most immune cell populations. There was significant up-regulation of the transcripts of both cytokines in the livers of Rag 1, γ common chain double knockout mice (wild-type control compared to wild-type APAP*p<0.001, Rag−/− γ/− control compared to Rag−/− γ/− APAP**p<0.001). (c-d) Culture of primary mouse endothelial cells from wild-type mice with DNA from apoptotic, but not healthy hepatocytes results in up-regulation of pro-IL-1β and pro-IL-18, and this is down-regulated by TLR9 antagonist ODN2088 (apoptotic DNA compared to apoptotic DNA with ODN2088 *p<0.001). (e-f) Culture of mouse endothelial cells from TLR9−/− mice with DNA from apoptotic and healthy hepatocytes does not result in up-regulation of pro-IL-1β and pro-IL-18. (g) To establish the importance of IL-1β in APAP hepatotoxicity an anti-IL-1β antibody (0.2 mg each) was used for in-vivo neutralization. This demonstrates significant increase in survival of wild-type mice in the presence of IL-1β neutralization compared to control antibody after APAP (control antibody n=10, anti-IL-1β n=10 P<0.02). (h) To establish the importance of IL-18 in APAP hepatotoxicity IL18−/− and wild-type mice were treated APAP. There was significantly better survival in IL-18−/− mice compared to wild-type (wild-type n=10, IL-18−/− n=7 P<0.036).
Figure 3:
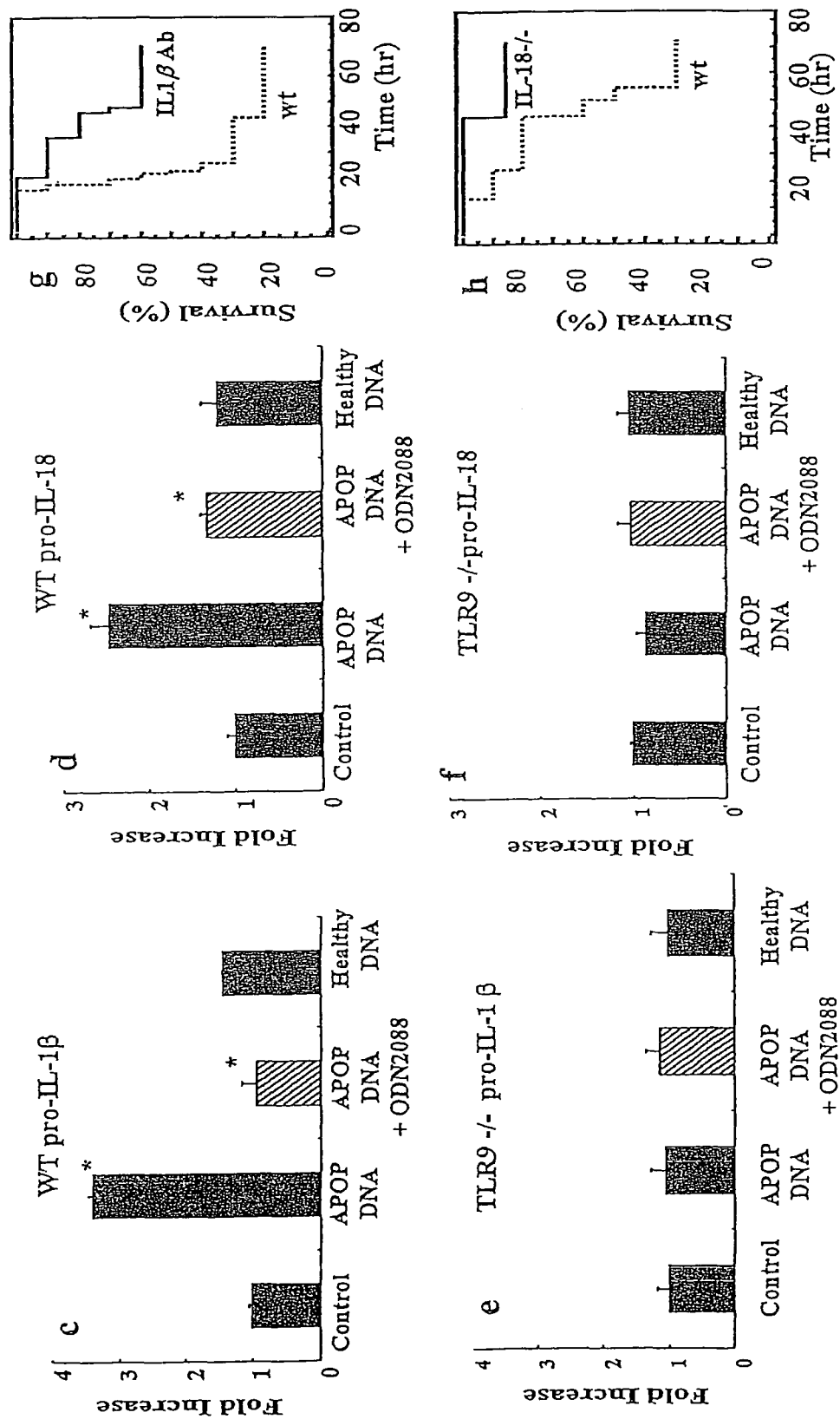

The inventors directly tested if DNA from apoptotic hepatocytes (50 μg/ml) can up-regulate pro-IL-1β and pro-IL-18 in liver sinusoidal endothelial cells from wild-type mice, and found significant up-regulation 24 hrs after culture (FIG. 3c-d). This up-regulation of pro-IL-1β and pro-IL-18 was inhibited by the TLR9 antagonist ODN2088, and did not occur in liver sinusoidal endothelial cells from TLR9−/− mice (FIG. 3e-f). To confirm in-vivo the importance of IL-1β and IL-18 in APAP induced hepatotoxicity we gave a single toxic dose of APAP in wild-type mice in which IL-1β had been neutralized, and also to mice deficient in IL-18. In the absence of either IL-1β or IL-18 there was significantly reduced mortality compared to wild-type mice in response to APAP (control antibody n=10, anti-IL-1β n=10 P<0.02) (wild-type n=10, IL-18−/− n=7 P<0.036) (FIG. 3g-h).

Reduced Mortality and Liver Injury in Mice Lacking Components of the NALP3 Inflammasome Pro-IL-1β and pro-IL-18 require cleavage to become biologically active, and this occurs predominantly by capsase-1 (10). This regulatory importance of caspase-1 is demonstrated by the fact that many cells constitutively synthesize pro-IL-18, but there is no functional IL-18 until cleavage and activation (26). The importance of caspase-1 in pro-IL-1β and pro-IL-18 processing have been known for some time, and recently the molecular components responsible for caspase-1 activation have been identified. These consist of a family of cytosolic proteins which form a complex called the inflammasome consisting of a NALP family member, the adaptor protein ASC and caspase-1 (17). The best characterized of the NALP molecules which can activate caspase1 is NALP3 which itself can be activated by monosodium urate (MSU) and ATP. Another NLR family member, IPAF, can also activate caspapse-1 in response to gram-negative bacteria.

Figure 4:
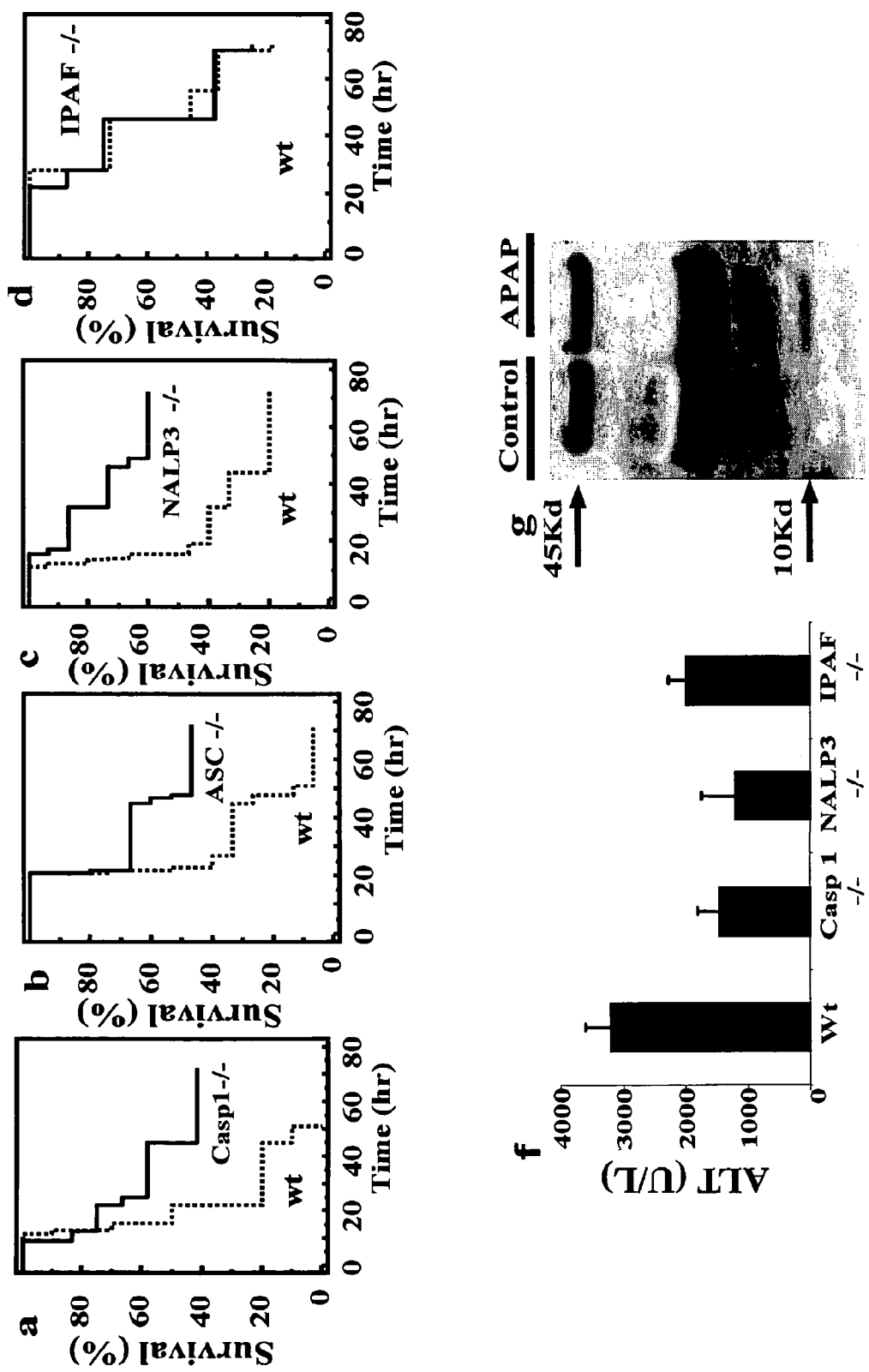
FIG. 4 shows that APAP-mediated hepatotoxicity is dependent on the NALP3, but not the IPAF inflammasome. (a) Survival of caspase 1−/− and controls after intraperitoneal injection of 500 mg/kg APAP (wild-type n=12, caspase 1−/− n=12 P<0.04) (b) Survival of ASC−/− and controls after APAP (wild-type n=15, ASC−/− n=15 P<0.03). (c) Survival of NALP3−/− and controls after APAP (wild-type n=15, NALP3−/− n=15 P<0.006). (d) Survival of IPAF−/− and controls after APAP (wild-type n=12, IPAF−/− n=8 P: NS). (e) H&E staining of livers at 20× magnification from wt, caspase 1−/−, ASC−/− and NALP3−/− mice 12 hrs after ip injection of PBS or APAP showing reduced necroinflammation and hemorrhage in all the mice lacking components of the NALP3 inflammasome. (f) Serum ALT from wild-type, Casp 1−/−, ASC−/−, NALP 3−/− and IPAF−/− 12 hrs after APAP. In Casp 1−/−, ASC−/− and NALP 3−/− serum ALT were significantly less than the wild-type after APAP (P<0.03) (g) To confirm in-vivo caspase-1 activation in endothelial cells, 24 hours after administration of APAP or control PBS liver sinusoidal cells were isolated and cleavage of caspase-1 detected by western blotting.
Figure 4:
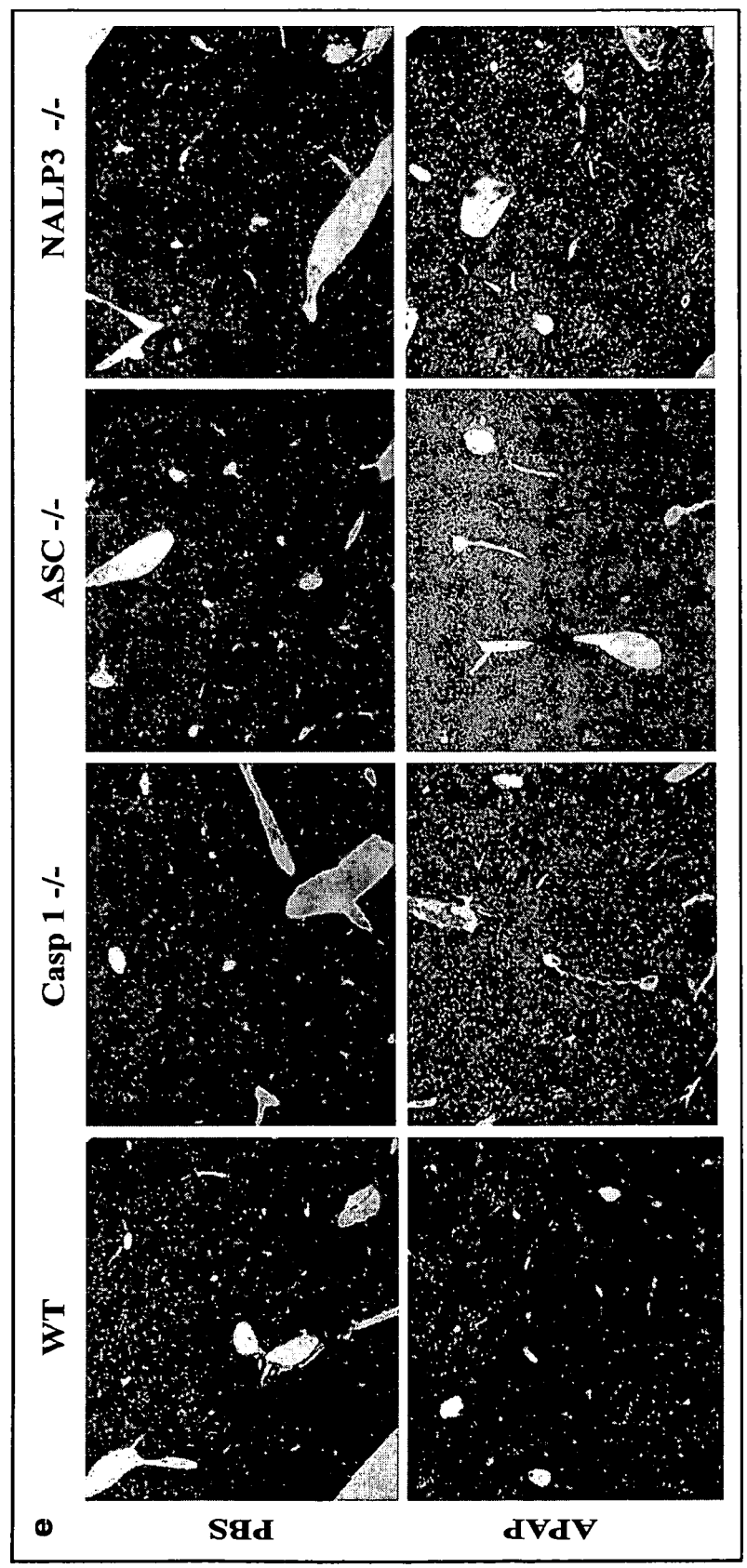

The important role of IL-1β and IL-18 in APAP induced hepatotoxicity and their dependence on caspase-1 for activation directed us to investigate the role of the caspase-1 pathway in APAP hepatotoxicity. We tested the requirement for components of the inflammasome using mice deficient in caspase-1, ASC, NALP3 or IPAF (caspase-1−/−, ASC−/−, NALP3−/−, and IPAF−/−). We found that caspase-1−/−, ASC−/− and NALP3−/− mice were significantly less susceptible to APAP induced injury than controls (FIG. 4a-c), but IPAF−/− mice were not protected (FIG. 4d) (wild-type n=12, caspase 1−/− n=12 P<0.04) (wild-type n=15, ASC−/− n=15 P<0.03) (wild-type n=15, NALP3−/− n=15 P<0.006) (wild-type n=12, IPAF−/− n=8 P: NS). Histological analysis showed that there was less liver injury in the absence of caspase-1, ASC or NALP3 (FIG. 4e). Measurement of serum ALT levels confirmed this by showing significantly reduced serum ALT in caspases-1−/− and NALP3−/− mice (P<0.03). This demonstrates a critical role for the NALP3 inflammasome pathway, and confirms the important role for IL-1β and IL-18 in APAP induced liver injury. The predominant expression of TLR9 in the liver is on sinusoidal endothelial cells, and it was therefore important to establish if there is caspase-1 cleavage in these cells during APAP induced hepatotoxicity. Indeed, twelve hours after APAP we isolated liver sinusoidal endothelial cells and western blot analysis performed showed cleavage of caspase-1 in these cells (FIG. 4g).

Aspirin Inhibits the Caspase-1 Pathway and Protects from APAP Induced Mortality

Figure 5:
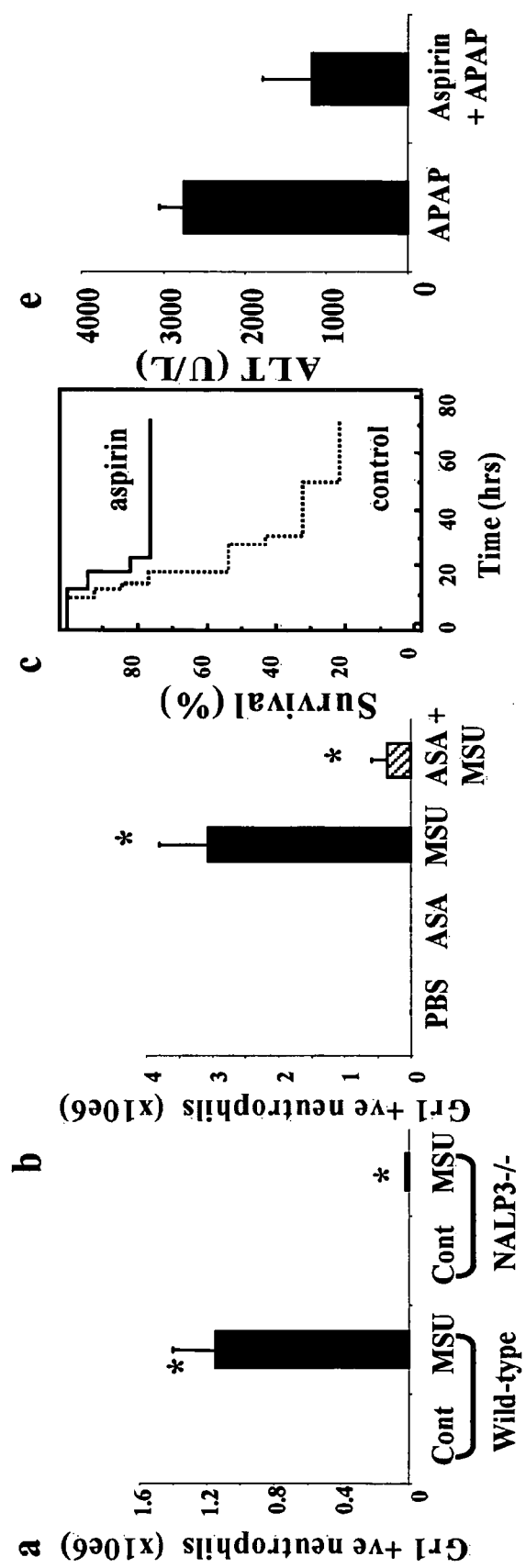
FIG. 5 Aspirin inhibits the NALP3 pathway and reduces APAP induced liver injury. (a) wild-type or NALP3−/− mice were injected with MSU crystals ip (3 mg/mouse). After 3 hours peritoneal lavage was performed and the number of GR-1 positive neutrophils quantified (wild-type MSU compared to NALP3 MSU*P<0.0001). (b) wild-type mice were treated with or without aspirin (60 mg/l) in the drinking water for 3 days and then injected intraperitoneally with MSU crystals or PBS. After 3 hours peritoneal lavage was performed and the number of Gr-1 positive neutrophils quantified (MSU compared to MSU+ASA*P<0.0001). (c) Survival analysis of mice treated with and without aspirin (60 mg/l) in the drinking water for 3 days and then injected intraperitoneally with APAP (500 mg/kg) (control drinking water n=13, aspirin drinking water n=17 P<0.02). (d) H&E stained liver tissue sections at 20× magnification from wild-type mice 12 hours after ip injection with APAP or PBS. Mice were on aspirin or regular drinking water for three days prior to APAP injection. There is significant reduction in APAP induced liver injury and hemorrhage in mice receiving aspirin. (e) Serum ALT from wild-type mice 12 hrs APAP with and without pretreatment with aspirin. The aspirin treated group had significantly lower serum ALT (P<0.04).
Figure 5:
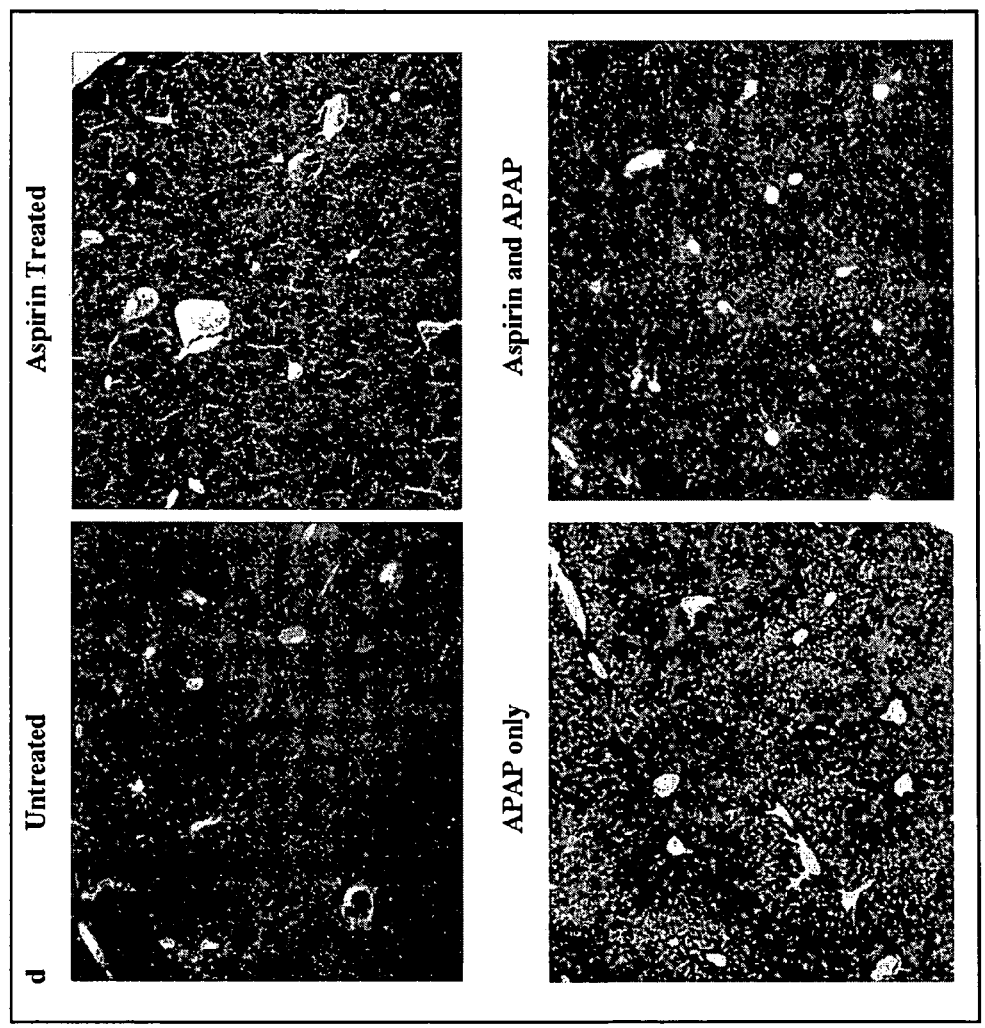

The above data has identified pathways critical for APAP hepatotoxicity which converge on caspase-1. One value of demonstrating new pathways in a disease process is that it can lead to novel therapies. In this context our goal was to identify a safe, anti-inflammatory agent that would inhibit the NALP3/ASC/caspase-1 pathway. This agent could have therapeutic potential in APAP induced hepatotoxicity, and possibly other types of liver injury. To test candidate drugs we utilized an established model of NALP3 inflammasome activation in which intraperitoneal injection (i.p.) of monosodium urate (MSU crystals) induces a neutrophilic peritonitis (27). First we confirmed that NALP3 was required in this model by testing in mice deficient in NALP3. As expected NALP3−/− mice had markedly less neutrophilic infiltrate at 3 hrs compared to wild-type mice challenged with MSU crystals (FIG. 5a). Then we tested if low dose aspirin, a widely available, inexpensive and safe drug could inhibit this pathway. We found an eightfold reduction in neutrophil exudates when mice were pre-treated with low dose aspirin in drinking water for three days prior to induction of MSU peritonitis (FIG. 5b). We next investigated whether low dose aspirin would protect against APAP induced liver injury. We found that low dose aspirin administration protected against APAP induced liver injury, as demonstrated by markedly improved survival and histology (control drinking water n=13, aspirin drinking water n=17 P<0.02) (FIG. 5c-d). When aspirin was given concordantly with APAP it still offered significant, though reduced, protection (Control 22% survival+/−19%, aspirin at 6 mg/kg survival 43%+/−11%, P<0.04).

Aspirin has a number of well characterized dose-dependent effects. At low dose (1-6 mg/kg/day) aspirin inhibits cox-1 and platelet degranulation, and recently has been found to regulate gene transcription (28). At higher doses there is inhibition of cox-2 and NFκB. The dose we used (4-6 mg/kg) was below that required for cox-2 and NFκB inhibition. Cox-2 inhibition is also known to increase rather than decrease APAP induced hepatotoxicity, and was therefore unlikley to be a mechanism for the protective effects of aspirin (29). We therefore tested if the protective effect of aspirin could be due to inhibition of cox-1 or platelet degranulation by administering the anti-platelet agent clopidogrel, or cox-1 inhibitor SC-560. Inhibition of platelet degranulation or cox-1 prior to APAP exposure did not protect mice against APAP toxicity (PBS gavage n=15, clopidogrel gavage n=15 P<0.31) (PBS gavage n=10, SC-560 gavage n=10 P<0.97) (FIG. 6a-b) suggesting that a novel mechanism accounted for the protective effects of low-dose aspirin.

Figure 6:
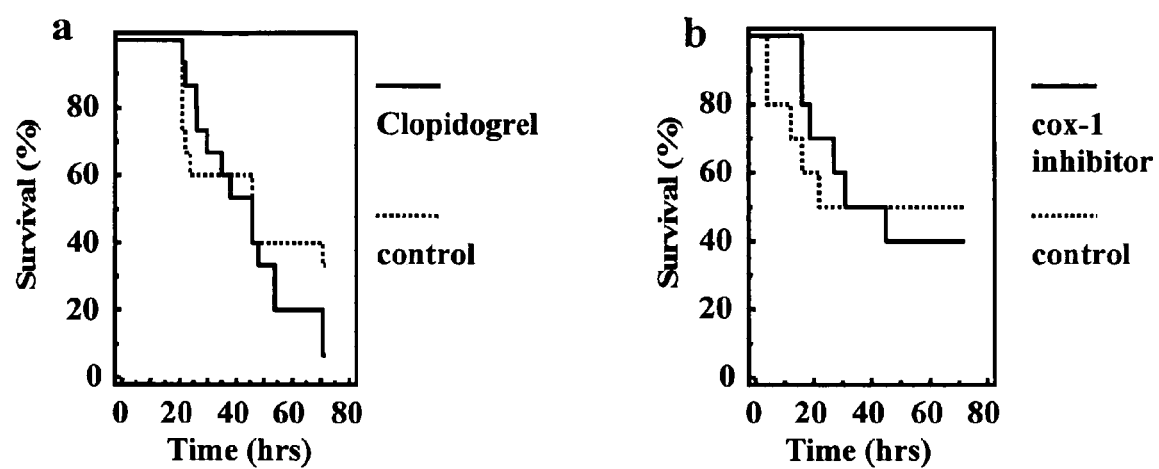
FIG. 6 Aspirin down-regulates pro-IL-1β and pro-IL-18 transcripts. (a) Survival after ip injection of APAP with and without clopidogrel by gavage (30 mg/kg every 24 hrs) (PBS gavage n=15, clopidogrel gavage n=15 P<0.31). Clopidogrel or PBS was gavaged every 24 hours beginning 48 hours prior and ending 24 hours after APAP injection. (b) Survival after ip injection of APAP with and without cox-1 inhibitor SC-560. SC-560 (5 mg/kg) or control PBS was gavaged twice daily beginning 60 hours prior and ending 48 hours after APAP injection (PBS gavage n=10, SC-560 gavage n=10 P<0.97). (c-f) Real-time PCR for pro-IL-1β, pro-IL-18, TNF-α and IFN-γ from whole livers of mice treated as describe above. Shown is a representative experiment out of four in which each group represents three mice (APAP compared to ASA+APAP for c and d*p<0.03, APAP compared to ASA+APAP for e and f**p<0.005). (g) ELISA for IL-1β from serum of mice given APAP with and without ASA in drinking water (APAP compared to ASA+APAP*p<0.02). (h) Real-time PCR for pro-IL-1β from THP-1 cells that were incubated overnight with control vehicle, or various doses of aspirin and then for 8 hours with or without LPS. Data shown is a representative experiment of three in which each treatment was performed in triplicate (LPS compared to LPS+ASA 1.5 mM* and LPS compared to LPS+ASA 0.15 mM # P<0.05).
Figure 6:
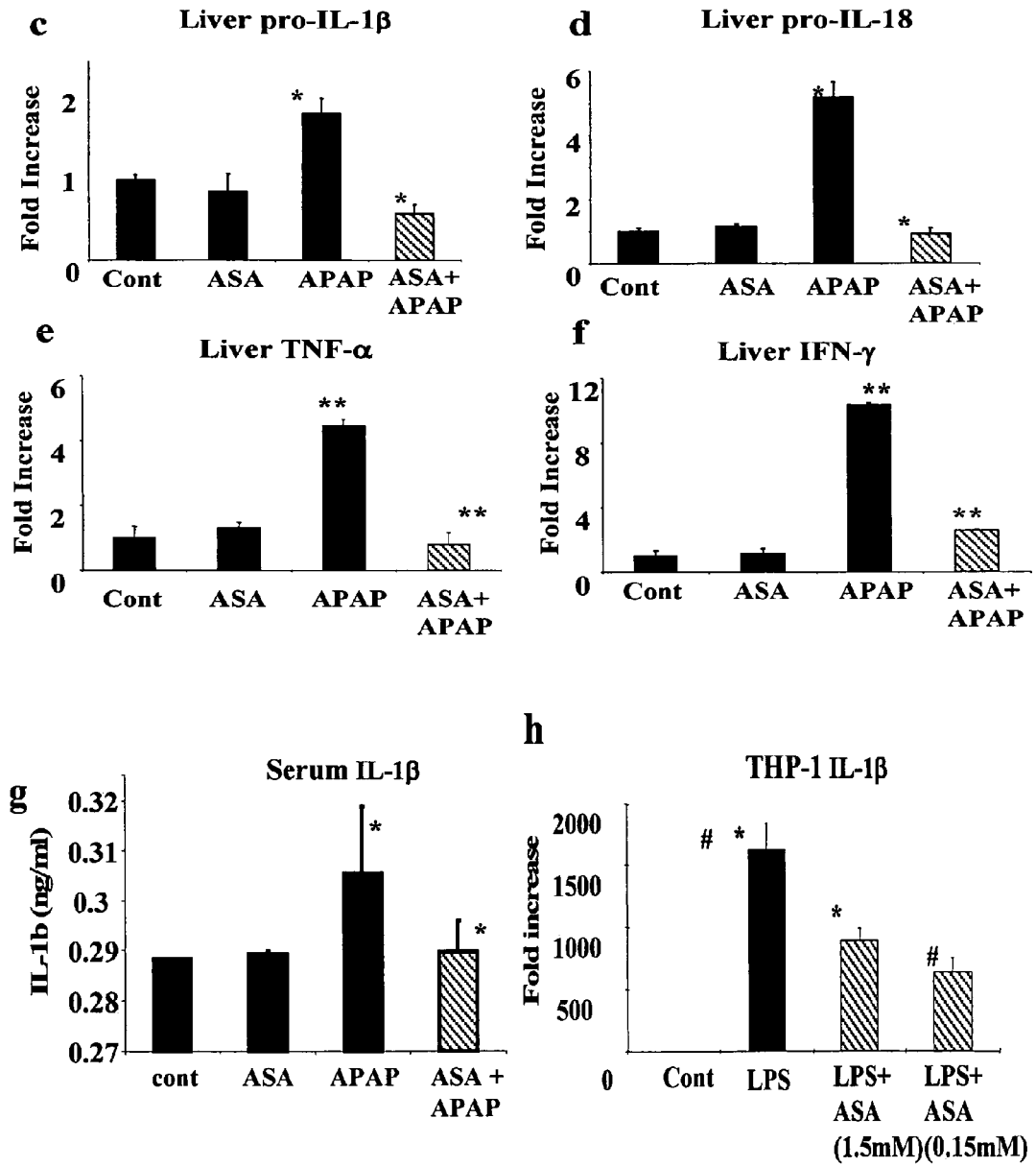
Figure 7:
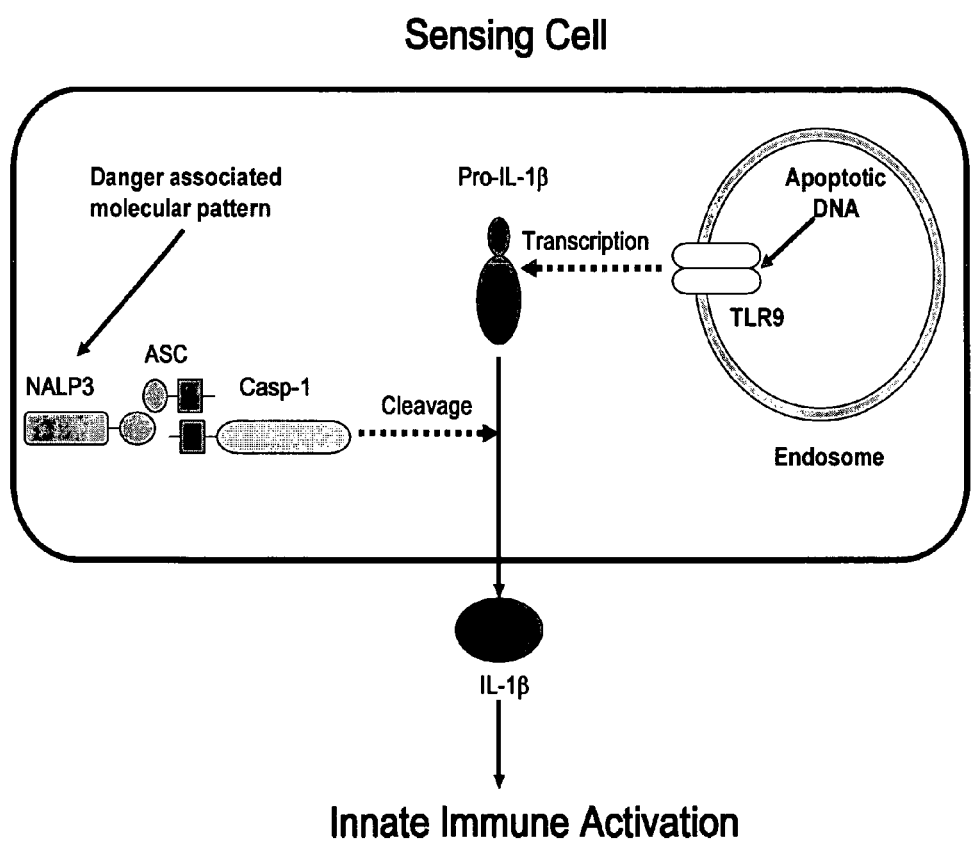
FIG. 7 shows production of mature IL-1β in APAP hepatotoxicity. Release of mature IL-1β requires transcription of pro-IL-1β, and subsequent cleavage and secretion by activated caspases-1. In APAP hepatotoxicity apoptotic mammalian DNA has been shown to increase transcription of pro-IL-1β via a TLR9 dependent pathway, and caspase-1 has been shown to be activated via a NALP3, ASC pathway. The identity of the presumed danger associated molecules responsible for activating the NALP3 inflammasome in APAP hepatotoxicity remains to be determined.

Due to the dependence of APAP toxicity on IL-1β and IL-18, and the recent demonstration of transcriptional down regulation of a number of genes by low dose aspirin we next examined if aspirin reduced the up-regulation of pro-IL-1β and pro-IL-18 transcripts induced by APAP(30). Using whole liver extracts we found the increase in pro-IL-1β and pro-IL-18 message by APAP hepatotoxicity was reduced to normal levels with aspirin pre-treatment (FIG. 6c-d). IL-1β and IL-18 are known to be potent stimulators of TNF-α and IFN-γ respectively, and we confirmed that expression of TNF-α and IFN-γ were also reduced by aspirin treatment (FIG. 6e-f). To confirm changes in IL-1β levels in-vivo we assayed serum IL-1β levels from mice treated with APAP, with and without ASA. As shown in FIG. 6g, ASA resulted in a significant reduction in the elevated IL-1β levels induced by APAP hepatotoxicity. To test if aspirin can directly reduce IL-1β levels we studied THP1 cells (human acute monocytic leukemia cell line) in-vitro. Activation of THP1 cells by LPS is known to result in up-regulation of pro-IL-1β transcript, and we demonstrate that this response was reduced by aspirin (FIG. 6h). Our data shows that aspirin reduced IL-1β and IL-18 through decreasing transcript levels and identifies a novel anti-inflammatory mechanism for aspirin.

Discussion

The present inventors have identified a two signal requirement for initiation of APAP induced liver toxicity. TLR9 provides a signal for the transcription of pro-IL-1β and pro-IL-18, and the NALP3 inflammasome provides the signal for cleavage and activation of these pro-cytokines. In addition we have demonstrated the biological significance of mammalian DNA from apoptotic cells in activating TLR9, expanding its known role as a stimulus for the development of autoimmunity to also inducing sterile inflammation (19, 23, 31).

Activation of TLR9 results in up-regulation of IL-1β and IL-18, and we have shown the importance of each of these cytokines by using neutralizing antibodies and genetically altered mice respectively. The findings presented herein support the recent report of the importance of IL1-R in the sterile inflammatory response, and demonstrate the importance of IL-1β as an upstream signal (7). The requirement for IL-18 in APAP induced liver injury is consistent with its known roles in immune activating and infectious models of liver injury, including concanavalin A and LPS injury after *Propionibacterium acnes* priming (32). This study further expands the role of IL-18, and demonstrates that it has an important and non-redundant role in the sterile inflammatory response to cellular death in the liver. In a model of sterile inflammation induced by intraperitoneal injection of necrotic cells Chen et. al., demonstrated that IL-1α was more important than IL-1β, and that IL-18 had a minimal role. The importance of IL-1β and IL-18 in the liver, but not the peritoneum highlights that pathways involved in the sterile inflammatory response have organ specificity, and this is likely due to the unique immune cellular composition of each organ. This conclusion is supported by the observed reduction in injury after myocardial infarction in the absence of caspase-1 activity (33).

Identification of DNA from apoptotic cells as an agonist for TLR9 in APAP hepatotoxicity has important therapeutic implications in the near future, and we have demonstrated that a TLR 7 and 9 antagonist currently in clinical development can improve survival from APAP toxicity (FIG. 2c). The signals for activation of the NALP3 inflammasome are less well identified than those required for TLR9, with uric acid and ATP from dying hepatocytes as candidates (34, 35). The relative importance of these for NALP3 activation in APAP hepatotoxicity needs to be established.

The model builds on the known mechanism of APAP induced toxic injury to hepatocytes and identifies DNA from apoptotic cells as a signal for immune activation. This model requires the presence of a sensing cell which detects and responds to the DNA from apoptosing cells. Such a cell would have to demonstrate up-regulation of pro-IL-β and pro-IL-18 in response to apoptotic DNA, and also caspase-1 activation in-vivo. The expression of TLR9 in the liver is predominantly on sinusoidal endothelial cells, and these were therefore prime candidates for the sensing cell population (24). We have shown that LSEC can be stimulated by mammalian apoptotic DNA in a TLR9 dependent manner to up-regulate pro-IL-1β and pro-IL-18, and that caspase-1 activation occurs in LSEC after APAP hepatotoxicity (FIG. 3c-f). The liver is however known to contain a very complex population of non-parenchymal cells including Kupffer cells, NK cells, NK-T cells, dendritic cells and stellate cells. There is very limited information on the response of these populations to TLR9 activation, although some are known to express TLR9 (23, 36). The role of these populations in sensing DNA from apoptotic cells remains to be established. In contrast to the response of liver non-parenchymal cells to TLR9 activation there is much better understanding for IL-1β and IL-18 in stimulating activation and cytotoxicity of liver non-parenchymal cells. This would place activation of non-parenchymal cells downstream of the production of IL-1β and IL-18.

This study also demonstrated that aspirin inhibits NALP3 inflammasome mediated inflammatory responses at a low dose (4-6 mg/kg) (FIG. 5b). Previously aspirin has been demonstrated to reduce liver injury, but not improve survival from APAP in mice and rats when given in a dose range toxic to humans (200-600 mg/kg) (37, 38). Such high doses are known to inhibit cox-2, and the subsequent demonstration that cox-2 is protective in APAP toxicity may be the reason for the inability of aspirin at these doses to improve mortality (29). Due to the lack of affect on mortality, and the toxic doses of aspirin there were no clinical implications for these earlier findings.

Inhibition of gene transcription is a recently recognized mechanism of action of aspirin, and this is the first demonstration of reduced transcription of inflammatory cytokines (28). This is of value because the known ability of aspirin to inhibit cox-1 and cox-2 does not explain its anti-inflammatory effects. Consistent with this, inhibition of cox-1, cox-2 and platelet degranulation do not protect against APAP hepatotoxicity. The requirement of NALP3 inflammasome mediated inflammation in APAP induced hepatotoxicity and the ability of aspirin to inhibit this pathway to the degree that it reduces liver injury and improves survival has significant clinical implications. If confirmed in humans, co-formulation of aspirin with APAP may reduce hepatotoxicity from APAP overdoses. Furthermore the NALP3 inflammasome may have an important role in other forms of sterile inflammation such as ischemic and non-alcoholic steatohepatitis.

REFERENCES

1. Lee, W. M. 2007. Acetaminophen toxicity: changing perceptions on a social/medical issue. *Hepatology* 46:966-970.
2. Kaplowitz, N. 2004. Acetaminophen hepatotoxicity: what do we know, what don't we know, and what do we do next? *Hepatology* 40:23-26.
3. Liu, Z. X., Han, D., Gunawan, B., and Kaplowitz, N. 2006. Neutrophil depletion protects against murine acetaminophen hepatotoxicity. *Hepatology* 43:1220-1230.
4. Liu, Z. X., Govindarajan, S., and Kaplowitz, N. 2004. Innate immune system plays a critical role in determining the progression and severity of acetaminophen hepatotoxicity. *Gastroenterology* 127:1760-1774.
5. Cover, C., Liu, J., Farhood, A., Malle, E., Waalkes, M. P., Bajt, M. L., and Jaeschke, H. 2006. Pathophysiological role of the acute inflammatory response during acetaminophen hepatotoxicity. *Toxicol Appl Pharmacol* 216:98-107.
6. Fiorucci, S., Antonelli, E., Mencarelli, A., Palazzetti, B., Alvarez-Miller, L., Muscara, M., del Soldato, P., Sanpaolo, L., Wallace, J. L., and Morelli, A. 2002. A NO-releasing derivative of acetaminophen spares the liver by acting at several checkpoints in the Fas pathway. *Br J Pharmacol* 135:589-599.
7. Chen, C. J., Kono, H., Golenbock, D., Reed, G., Akira, S., and Rock, K. L. 2007. Identification of a key pathway required for the sterile inflammatory response triggered by dying cells. *Nat Med* 13:851-856.
8. Mariathasan, S., Newton, K., Monack, D. M., Vucic, D., French, D. M., Lee, W. P., Roose-Girma, M., Erickson, S., and Dixit, V. M. 2004. Differential activation of the inflammasome by caspase-1 adaptors ASC and Ipaf. *Nature* 430: 213-218.
9. Martinon, F., Burns, K., and Tschopp, J. 2002. The inflammasome: a molecular platform triggering activation of inflammatory caspases and processing of proIL-beta. *Mol Cell* 10:417-426.
10. Ogura, Y., Sutterwala, F. S., and Flavell, R. A. 2006. The inflammasome: first line of the immune response to cell stress. *Cell* 126:659-662.
11. Vollmer, J. 2006. TLR9 in health and disease. *Int Rev Immunol* 25:155-181.
12. Lamphier, M. S., Sirois, C. M., Verma, A., Golenbock, D. T., and Latz, E. 2006. TLR9 and the recognition of self and non-self nucleic acids. *Ann NY Acad Sci* 1082:31-43.
13. Enari, M., Sakahira, H., Yokoyama, H., Okawa, K., Iwamatsu, A., and Nagata, S. 1998. A caspase-activated DNase that degrades DNA during apoptosis, and its inhibitor ICAD. *Nature* 391:43-50.
14. Huck, S., Deveaud, E., Namane, A., and Zouali, M. 1999. Abnormal DNA methylation and deoxycytosine-deoxyguanine content in nucleosomes from lymphocytes undergoing apoptosis. *Faseb J* 13:1415-1422.
15. Lunec, J., Herbert, K., Blount, S., Griffiths, H. R., and Emery, P. 1994. 8-Hydroxydeoxyguanosine. A marker of oxidative DNA damage in systemic lupus erythematosus. *FEBS Lett* 348:131-138.
16. Rifkin, I. R., Leadbetter, E. A., Busconi, L., Viglianti, G., and Marshak-Rothstein, A. 2005. Toll-like receptors, endogenous ligands, and systemic autoimmune disease. *Immunol Rev* 204:27-42.
17. Mariathasan, S., and Monack, D. M. 2007. Inflammasome adaptors and sensors: intracellular regulators of infection and inflammation. *Nat Rev Immunol* 7:31-40.
18. Barrat, F. J., Meeker, T., Chan, J. H., Guiducci, C., and Coffman, R. L. 2007. Treatment of lupus-prone mice with a dual inhibitor of TLR7 and TLR9 leads to reduction of autoantibody production and amelioration of disease symptoms. *Eur J Immunol* 37:3582-3586.

19. Barrat, F. J., Meeker, T., Gregorio, J., Chan, J. H., Uematsu, S., Akira, S., Chang, B., Duramad, O., and Coffman, R. L. 2005. Nucleic acids of mammalian origin can act as endogenous ligands for Toll-like receptors and may promote systemic lupus erythematosus. *J Exp Med* 202: 1131-1139.
20. Dinarello, C. A. 2007. Interleukin-18 and the pathogenesis of inflammatory diseases. *Semin Nephrol* 27:98-114.
21. Pirhonen, J., Sareneva, T., Kurimoto, M., Julkunen, I., and Matikainen, S. 1999. Virus infection activates IL-1 beta and IL-18 production in human macrophages by a caspase-1-dependent pathway. *J Immunol* 162:7322-7329.
22. Kalina, U., Koyama, N., Hosoda, T., Nuernberger, H., Sato, K., Hoelzer, D., Herweck, F., Manigold, T., Singer, M. V., Rossol, S., et al. 2002. Enhanced production of IL-18 in butyrate-treated intestinal epithelium by stimulation of the proximal promoter region. *Eur J Immunol* 32:2635-2643.
23. Watanabe, A., Hashmi, A., Gomes, D. A., Town, T., Badou, A., Flavell, R. A., and Mehal, W. Z. 2007. Apoptotic hepatocyte DNA inhibits hepatic stellate cell chemotaxis via toll-like receptor 9. *Hepatology* 46:1509-1518.
24. Martin-Arenas, M., Simon-Santamaria, J., Pettersen, I., Moens, U., Smedsrod, B., and Sveinbjornsson, B. 2006. Toll-like receptor 9 (TLR9) is present in murine liver sinusoidal endothelial cells (LSECs) and mediates the effect of CpG-oligonucleotides. *J Hepatol* 44:939-946.
25. Traggiai, E., Chicha, L., Mazzucchelli, L., Bronz, L., Piffaretti, J. C., Lanzavecchia, A., and Manz, M. G. 2004. Development of a human adaptive immune system in cord blood cell-transplanted mice. *Science* 304:104-107.
26. Puren, A. J., Fantuzzi, G., and Dinarello, C. A. 1999. Gene expression, synthesis, and secretion of interleukin 18 and interleukin 1beta are differentially regulated in human blood mononuclear cells and mouse spleen cells. *Proc Natl Acad Sci USA* 96:2256-2261.
27. Martinon, F., Petrilli, V., Mayor, A., Tardivel, A., and Tschopp, J. 2006. Gout-associated uric acid crystals activate the NALP3 inflammasome. *Nature* 440:237-241.
28. Wu, K. K., Liou, J. Y., and Cieslik, K. 2005. Transcriptional Control of COX-2 via C/EBPbeta. *Arterioscler Thromb Vasc Biol* 25:679-685.
29. Reilly, T. P., Brady, J. N., Marchick, M. R., Bourdi, M., George, J. W., Radonovich, M. F., Pise-Masison, C. A., and Pohl, L. R. 2001. A protective role for cyclooxygenase-2 in drug-induced liver injury in mice. *Chem Res Toxicol* 14:1620-1628.
30. Wu, K. K. 2003. Aspirin and other cyclooxygenase inhibitors: new therapeutic insights. *Semin Vasc Med* 3:107-112.
31. Viglianti, G. A., Lau, C. M., Hanley, T. M., Miko, B. A., Shlomchik, M. J., and Marshak-Rothstein, A. 2003. Activation of autoreactive B cells by CpG dsDNA. *Immunity* 19:837-847.
32. Tsutsui, H., Matsui, K., Okamura, H., and Nakanishi, K. 2000. Pathophysiological roles of interleukin-18 in inflammatory liver diseases. *Immunol Rev* 174:192-209.
33. Pomerantz, B. J., Reznikov, L. L., Harken, A. H., and Dinarello, C. A. 2001. Inhibition of caspase 1 reduces human myocardial ischemic dysfunction via inhibition of IL-18 and IL-1 beta. *Proc Natl Acad Sci USA* 98:2871-2876.
34. Akahoshi, T., Murakami, Y., and Kitasato, H. 2007. Recent advances in crystal-induced acute inflammation. *Curr Opin Rheumatol* 19:146-150.
35. Duncan, J. A., Bergstralh, D. T., Wang, Y., Willingham, S. B., Ye, Z., Zimmermann, A. G., and Ting, J. P. 2007. Cryopyrin/NALP3 binds ATP/dATP, is an ATPase, and requires ATP binding to mediate inflammatory signaling. *Proc Natl Acad Sci USA* 104:8041-8046.
36. Tsujimoto, H., Ono, S., Matsumoto, A., Kawabata, T., Kinoshita, M., Majima, T., Hiraki, S., Seki, S., Moldawer, L. L., and Mochizuki, H. 2006. A critical role of CpG motifs in a murine peritonitis model by their binding to highly expressed toll-like receptor-9 on liver NKT cells. *J Hepatol* 45:836-843.
37. Whitehouse, L. W., Paul, C. J., and Thomas, B. H. 1976. Effect of acetylsalicylic acid on a toxic dose of acetaminophen in the mouse. *Toxicol Appl Pharmacol* 38:571-582.
38. De Vries, J., De Jong, J., Lock, F. M., Van Bree, L., Mullink, H., and Veldhuizen, R. W. 1984. Protection against paracetamol-induced hepatotoxicity by acetylsalicylic acid in rats. *Toxicology* 30:297-304.
39. Kuida, K., Lippke, J. A., Ku, G., Harding, M. W., Livingston, D. J., Su, M. S., and Flavell, R. A. 1995. Altered cytokine export and apoptosis in mice deficient in interleukin-1 beta converting enzyme. *Science* 267:2000-2003.
40. Sutterwala, F. S., Ogura, Y., Szczepanik, M., Lara-Tejero, M., Lichtenberger, G. S., Grant, E. P., Bertin, J., Coyle, A. J., Galan, J. E., Askenase, P. W., et al. 2006. Critical role for NALP3/CIAS1/Cryopyrin in innate and adaptive immunity through its regulation of caspase-1. *Immunity* 24:317-327.
41. Schmassmann, A., Zoidl, G., Peskar, B. M., Waser, B., Schmassmann-Suhijar, D., Gebbers, J. O., and Reubi, J. C. 2006. Role of the different isoforms of cyclooxygenase and nitric oxide synthase during gastric ulcer healing in cyclooxygenase-1 and -2 knockout mice. *Am J Physiol Gastrointest Liver Physiol* 290:G747-756.

The invention claimed is:

1. A pharmaceutical composition comprising a therapeutically effective amount of a hepatotoxicity inducing bioactive agent in combination with an effective amount of a salicylate according to the chemical structure:

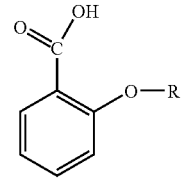

where R is H or a $C_2$-$C_{10}$ acyl group, or a pharmaceutically acceptable salt thereof, in combination with a pharmaceutically acceptable carrier, additive or excipient wherein the amount of said salicylate in said composition substantially reduces the hepatotoxicity of said bioactive agent after administration to a patient wherein said hepatotoxicity inducing bioactive agent is adriamycin (doxorubicin).

2. The composition according to claim 1 wherein R is an acetyl group.

3. The composition according to claim 1 wherein said salicylate increases the therapeutic index of said bioactive agent at least about 5-10% above the therapeutic index exhibited by said bioactive agent when administered in the absence of said salicylate.

4. The composition according to claim 1 wherein R is a $C_2$ acyl group.

5. The composition according to 1 wherein said salicylate is acetylsalicylic acid or a pharmaceutically acceptable salt thereof.

6. The composition according to claim 1 wherein said bioactive agent is included in said composition at a high effective dose.

7. The composition according to claim 1 wherein said salicylate compound is administered in sustained or controlled release form.

8. The composition according to claim 1 wherein said salicylate compound and said bioactive agent are delivered in sustained or controlled release form.

9. The composition according to claim 1 in oral dosage form.

10. The composition according to claim 1 in parenteral dosage form.

11. The composition according to claim 1 in buccal or sublingual dosage form.

12. The composition according to claim 1 in transdermal dosage form.

13. The composition according to claim 2 wherein said bioactive agent is included in said composition at a high effective dose.

14. The composition according to claim 2 wherein said salicylate compound is administered in sustained or controlled release form.

15. The composition according to claim 2 wherein said salicylate compound and said bioactive agent are delivered in sustained or controlled release form.

16. The composition according to claim 2 in oral dosage form.

17. The composition according to claim 2 in parenteral dosage form.

18. The composition according to claim 2 in buccal or sublingual dosage form.

19. The composition according to claim 2 in transdermal dosage form.

20. The composition of claim 7 in oral dosage form.

21. The composition of claim 8 in oral dosage form.

* * * * *